(12) United States Patent
Hegde et al.

(10) Patent No.: US 7,909,037 B2
(45) Date of Patent: Mar. 22, 2011

(54) TETHERED AIRWAY IMPLANTS AND METHODS OF USING THE SAME

(75) Inventors: Anant V. Hegde, Hayward, CA (US);
Kasey Kai-Chi Li, Palo Alto, CA (US);
Nikhil D. Bhat, Fremont, CA (US);
Doyeon Kim, Fremont, CA (US);
George Y. Choi, Redwood City, CA (US)

(73) Assignee: Pavad Medical, Fremont, CA (US)

( * ) Notice: Subject to any disclaimer, the term of this patent is extended or adjusted under 35 U.S.C. 154(b) by 399 days.

(21) Appl. No.: 11/737,107

(22) Filed: Apr. 18, 2007

(65) Prior Publication Data
US 2007/0246052 A1 Oct. 25, 2007

Related U.S. Application Data

(60) Provisional application No. 60/745,254, filed on Apr. 20, 2006.

(51) Int. Cl.
| | |
|---|---|
| *A61F 5/56* | (2006.01) |
| *A61F 13/00* | (2006.01) |
| *A61F 5/04* | (2006.01) |
| *A61F 2/30* | (2006.01) |
| *A61F 2/00* | (2006.01) |
| *A61B 19/00* | (2006.01) |
| *A61B 17/56* | (2006.01) |
| *A61B 17/58* | (2006.01) |
| *A61B 17/70* | (2006.01) |

(52) U.S. Cl. ........ 128/848; 128/846; 128/897; 128/899; 602/902; 606/53; 606/60; 606/263; 606/264; 600/37

(58) Field of Classification Search .................. 128/848, 128/846, 860, 897, 899; 602/902; 606/53, 606/60, 250, 251, 254, 260, 263, 264; 600/37
See application file for complete search history.

(56) References Cited

U.S. PATENT DOCUMENTS
5,176,618 A 1/1993 Freedman
(Continued)

OTHER PUBLICATIONS

U.S. Appl. No. 12/072,680, filed Feb. 27, 2008, Doelling et al.

*Primary Examiner* — Patricia M Bianco
*Assistant Examiner* — Brandon Jackson
(74) *Attorney, Agent, or Firm* — Kilpatrick Townsend & Stockton LLP

(57) ABSTRACT

An airway implant device for maintaining and/or creating an opening in air passageways is disclosed. Methods of using the device are also disclosed. The airway implant device includes a deformable element to control the opening of an air passageway and a tether. Preferably the deformable element is an electroactive polymer element. Energizing of the electroactive polymer element provides support for the walls of an air passageway, when the walls collapse, and thus, completely or partially opens the air passageway. Also disclosed is an implant for stabilizing the tongue, the implant having an anchoring portion for securing a first end of the implant with the mandibula; a control portion connected with the anchoring portion, configured for selectively activating the implant; a flexible portion connected at its proximal end with the control portion, where the flexible portion has three-dimensional flexibility in a first state and where the flexible portion has a lesser three-dimensional flexibility in a second state, and where the flexible portion is selectively switchable between the first and second state by the control portion; and an anchoring portion for connecting the implant with the base of the tongue connected with the distal end of the flexible portion. Methods of treating airway disorders such as sleep apnea and snoring with the airway implant device are disclosed herein.

13 Claims, 34 Drawing Sheets

U.S. PATENT DOCUMENTS

| | | |
|---|---|---|
| 5,979,456 A | 11/1999 | Magovern |
| 6,955,172 B2 | 10/2005 | Nelson et al. |
| 7,073,505 B2 | 7/2006 | Nelson et al. |
| 7,188,627 B2 | 3/2007 | Nelson et al. |
| 7,216,648 B2 | 5/2007 | Nelson et al. |
| 7,360,542 B2 | 4/2008 | Nelson et al. |
| 7,367,340 B2 | 5/2008 | Nelson et al. |
| 2005/0159637 A9 | 7/2005 | Nelson et al. |
| 2006/0058792 A1* | 3/2006 | Hynes .............................. 606/61 |
| 2007/0186936 A1 | 8/2007 | Nelson et al. |
| 2008/0066764 A1 | 3/2008 | Paraschac et al. |
| 2008/0066765 A1 | 3/2008 | Paraschac et al. |
| 2008/0066766 A1 | 3/2008 | Paraschac et al. |
| 2008/0066767 A1 | 3/2008 | Paraschac et al. |
| 2008/0066769 A1* | 3/2008 | Dineen et al. ................. 128/897 |

* cited by examiner

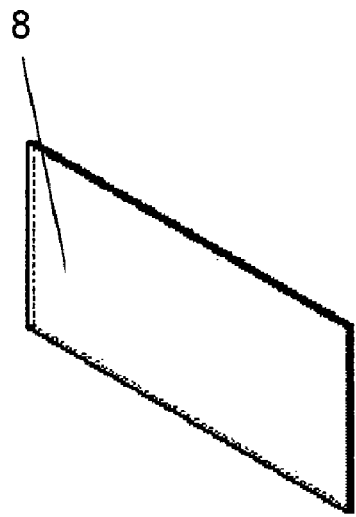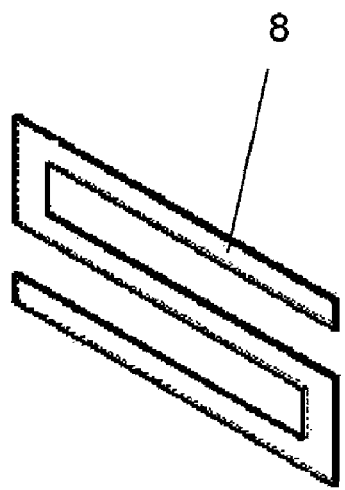
Fig. 9                Fig. 10
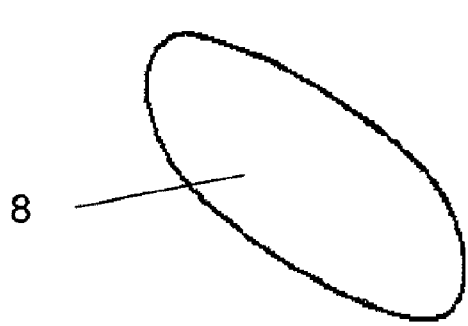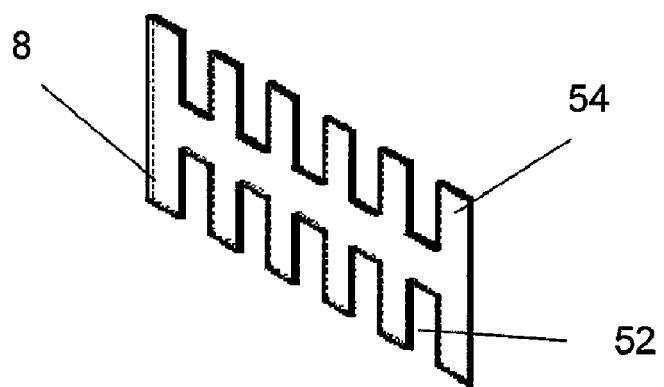
Fig. 11                Fig. 12

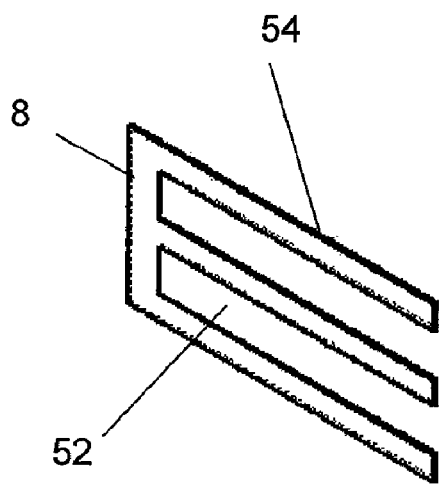 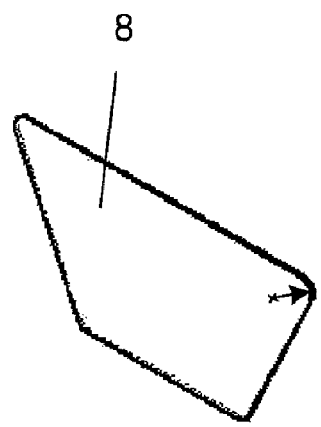
Fig. 13          Fig. 14
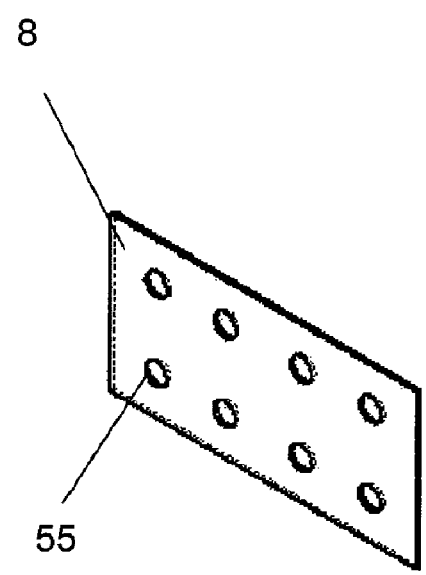 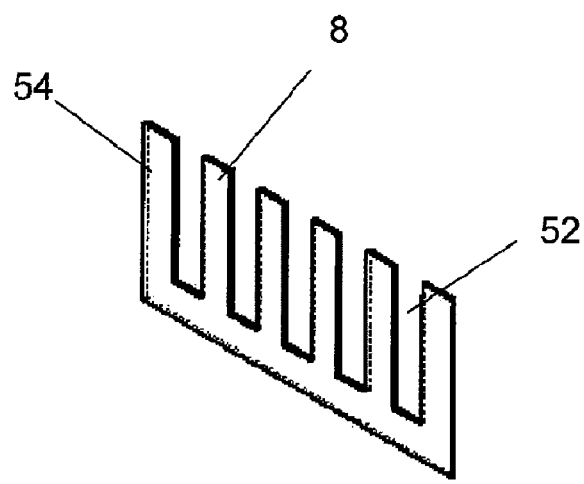
Fig. 15          Fig. 16

A    B    C $g_{ref}$ = reference gap to be maintained
$g_{act}$ = actual gap measured by the sensor

TETHERED AIRWAY IMPLANTS AND METHODS OF USING THE SAME

CROSS-REFERENCES TO RELATED APPLICATIONS

The present application claims priority to U.S. Provisional Patent Application No. 60/745,254, filed Apr. 20, 2006, the teachings of which are incorporated herein by reference.

BACKGROUND OF THE INVENTION

Snoring is very common among mammals including humans. Snoring is a noise produced while breathing during sleep due to the vibration of the soft palate and uvula. Not all snoring is bad, except it bothers the bed partner or others near the person who is snoring. If the snoring gets worst overtime and goes untreated, it could lead to apnea.

Those with apnea stop breathing in their sleep, often hundreds of times during the night. Usually apnea occurs when the throat muscles and tongue relax during sleep and partially block the opening of the airway. When the muscles of the soft palate at the base of the tongue and the uvula relax and sag, the airway becomes blocked, making breathing labored and noisy and even stopping it altogether. Sleep apnea also can occur in obese people when an excess amount of tissue in the airway causes it to be narrowed.

In a given night, the number of involuntary breathing pauses or "apneic events" may be as high as 20 to 60 or more per hour. These breathing pauses are almost always accompanied by snoring between apnea episodes. Sleep apnea can also be characterized by choking sensations.

Sleep apnea is diagnosed and treated by primary care physicians, pulmonologists, neurologists, or other physicians with specialty training in sleep disorders. Diagnosis of sleep apnea is not simple because there can be many different reasons for disturbed sleep.

The specific therapy for sleep apnea is tailored to the individual patient based on medical history, physical examination, and the results of polysomnography. Medications are generally not effective in the treatment of sleep apnea. Oxygen is sometimes used in patients with central apnea caused by heart failure. It is not used to treat obstructive sleep apnea.

Nasal continuous positive airway pressure (CPAP) is the most common treatment for sleep apnea. In this procedure, the patient wears a mask over the nose during sleep, and pressure from an air blower forces air through the nasal passages. The air pressure is adjusted so that it is just enough to prevent the throat from collapsing during sleep. The pressure is constant and continuous. Nasal CPAP prevents airway closure while in use, but apnea episodes return when CPAP is stopped or it is used improperly. Many variations of CPAP devices are available and all have the same side effects such as nasal irritation and drying, facial skin irritation, abdominal bloating, mask leaks, sore eyes, and headaches. Some versions of CPAP devices vary the pressure to coincide with the person's breathing pattern, and other CPAP devices start with low pressure, slowly increasing it to allow the person to fall asleep before the full prescribed pressure is applied.

Dental appliances that reposition the lower jaw and the tongue have been helpful to some patients with mild to moderate sleep apnea or who snore but do not have apnea. A dentist or orthodontist is often the one to fit the patient with such a device.

Some patients with sleep apnea may need surgery. Although several surgical procedures are used to increase the size of the airway, none of them is completely successful or without risks. More than one procedure may need to be tried before the patient realizes any benefits. Some of the more common procedures include removal of adenoids and tonsils (especially in children), nasal polyps or other growths, or other tissue in the airway and correction of structural deformities. Younger patients seem to benefit from these surgical procedures more than older patients.

Uvulopalatopharyngoplasty (UPPP) is a procedure used to remove excess tissue at the back of the throat (tonsils, uvula, and part of the soft palate). The success of this technique may range from 30 to 60 percent. The long-term side effects and benefits are not known, and it is difficult to predict which patients will do well with this procedure.

Laser-assisted uvulopalatoplasty (LAUP) is done to eliminate snoring but has not been shown to be effective in treating sleep apnea. This procedure involves using a laser device to eliminate tissue in the back of the throat. Like UPPP, LAUP may decrease or eliminate snoring but not eliminate sleep apnea itself. Elimination of snoring, the primary symptom of sleep apnea, without influencing the condition may carry the risk of delaying the diagnosis and possible treatment of sleep apnea in patients who elect to have LAUP. To identify possible underlying sleep apnea, sleep studies are usually required before LAUP is performed.

Somnoplasty is a procedure that uses RF to reduce the size of some airway structures such as the uvula and the back of the tongue. This technique helps in reducing snoring and is being investigated as a treatment for apnea.

Tracheostomy is used in persons with severe, life-threatening sleep apnea. In this procedure, a small hole is made in the windpipe and a tube is inserted into the opening. This tube stays closed during waking hours and the person breathes and speaks normally. It is opened for sleep so that air flows directly into the lungs, bypassing any upper airway obstruction. Although this procedure is highly effective, it is an extreme measure that is rarely used.

Patients in whom sleep apnea is due to deformities of the lower jaw may benefit from surgical reconstruction. Surgical procedures to treat obesity are sometimes recommended for sleep apnea patients who are morbidly obese. Behavioral changes are an important part of the treatment program, and in mild cases behavioral therapy may be all that is needed. Overweight persons can benefit from losing weight. Even a 10 percent weight loss can reduce the number of apneic events for most patients. Individuals with apnea should avoid the use of alcohol and sleeping pills, which make the airway more likely to collapse during sleep and prolong the apneic periods. In some patients with mild sleep apnea, breathing pauses occur only when they sleep on their backs. In such cases, using pillows and other devices that help them sleep in a side position may be helpful.

Recently, Restore Medical, Inc., Saint Paul, Minn. has developed a new treatment for snoring and apnea, called the Pillar technique. Pillar System involves a procedure where 2 or 3 small polyester rod devices are placed in the patient's soft palate. The Pillar System stiffens the palate, reduces vibration of the tissue, and prevents the possible airway collapse. Stiff implants in the soft palate, however, could hinder patient's normal functions like speech, ability to swallow, coughing and sneezing. Protrusion of the modified tissue into the airway is another long-term concern.

As the current treatments for snoring and/or apnea are not effective and have side-effects, there is a need for additional treatment options.

BRIEF SUMMARY OF THE INVENTION

Methods and devices for the treatment of airway disorders, such as snoring and/or apnea are disclosed herein. The device described herein comprises a deformable element. The deformable element is partially or completely implanted in an airway passageway wall or adjacent to an air passageway wall to treat the improper opening and closing of the passageway. In preferred embodiments, the deformable element is an electroactive polymer (EAP) element. The deformable element is typically inserted into the soft palate and/or sidewalls of the patient's airway. In one embodiment, the EAP element has a low stiffness under normal conditions. The EAP element is energized when the opening of the air passageway has to be maintained open, such as during sleep. When the EAP element is energized, the polymer stiffens and tends to deform and thus has the ability to support the weight of the soft palate and sidewalls of the air ways and open the air passageways. When the charge is removed, the EAP element becomes soft and tends not to interfere with the patient's normal activities like swallowing and speech. The airway implant devices described herein may completely or partially open the relevant air passageways.

One or more implants are placed in the soft palate, sidewalls of the airway, around the trachea, in the tongue, in the uvula, or in combinations thereof. The implant has lead wires (e.g., anode and cathode) attached to the EAP element. In some embodiments, the lead wires are connected to an induction coil. The induction coil is typically implanted in the roof of the mouth. Preferably, the patient wears a retainer type of device before going to bed. The retainer has an induction coil, a circuit and a battery. When the patient wears the retainer, the induction coil in the retainer is proximal to the induction coil that is implanted in the roof of the mouth. The energy is then transmitted through the tissue and to the coil that is in the roof of the mouth. When the EAP element is energized it deforms and/or stiffens to provide support to so as to completely or partially open the airways. In the morning when the patient wakes up, the patient removes the retainer and places the retainer on a charging unit to recharge the battery.

A first aspect of the invention is an airway implant device comprising an electroactive polymer element which is adapted and configured to modulate the opening of an air passageway. In some embodiments the device includes an anode and a cathode connected to the electroactive polymer element, an inductor, and a controller. The controller can be a microprocessor which is adapted and configured to sense the opening of the air passageway and control the energizing of the electroactive polymer element. Other embodiments of the device include a non-implanted portion, such as a mouth guard. Preferably, the non-implanted portion is adapted and configured to control the electroactive polymer element. The non-implanted portion also typically includes a power supply and an inductor. The inductor in the implanted portion is adapted and configured to interact with the inductor in the implanted portion of the device. The device is preferably adapted and configured for implantation into a soft palate and/or a lateral pharyngeal wall. In preferred embodiments, the electroactive polymer element comprises an ion-exchange polymer metal composite. The functioning of the device is preferably by energizing the electroactive polymer element which then causes a complete or partial opening of the air passageway. Preferably, the device comprises an inductive coupling mechanism adapted to connect the electroactive polymer element to a power source.

Other aspects of the invention are methods of using the devices disclosed herein. One embodiment is a method of controlling an opening of an air passageway by implanting an airway implant device comprising an electroactive polymer element proximal to an air passageway and/or in a wall of an air passageway and controlling the opening of the air passageway by energizing the electroactive polymer element to completely or partially open said air passageway. Preferably the control of the opening of the air passageway is in response to feedback from the air passageway regarding the opening of the air passageway. The airway implant device can be implanted in a soft palate and/or a lateral pharyngeal wall. Preferably, the airway implant device is controlled by an inductive coupling mechanism. This method is preferably used to treat airway disorders such as obstructive sleep apnea or snoring.

Another embodiment is a method of treating a disease using an airway implant device comprising implanting an airway implant device with a deformable element in the soft palate of a patient and controlling the opening of the air passageway by energizing the deformable element. The energizing of the deformable element moves the soft palate to support a collapsed tongue or a tongue that has the tendency to collapse and completely or partially opens the air passageway. The deformable element is preferably a non-magnetic material and even more preferably an electroactive polymer.

Yet another embodiment is a method of treating a disease using an airway implant device comprising implanting an airway implant device with a deformable element in a lateral pharyngeal wall and controlling the opening of the air passageway by energizing the deformable element, wherein the energizing of the deformable element supports the lateral pharyngeal wall and completely or partially opens the air passageway. The deformable element is preferably a non-magnetic material and even more preferably an electroactive polymer.

In one aspect of the invention the airway implant device further comprises a sensor element. The sensor element monitors the condition of the airway. Preferably, this monitoring of the airway is used to predict the occurrence of an apneic event or a snoring event. The sensor element can be in the same unit as the airway implant or can be in a separate unit. The sensor element can be implanted proximal to or in an airway wall. The sensor element, in some embodiments, provides feedback based on the monitoring directly or indirectly to the deformable element. The actuation of the deformable element in these embodiments is typically related to the feedback from the sensor element. In some embodiments, the deformable element functions as the sensor element. One embodiment of the invention is an airway implant device comprising a deformable element and a sensor element, wherein the deformable element is adapted and configured to modulate an opening of an air passageway and the sensor element is adapted and configured to monitor a condition of an airway to determine the likelihood of an apneic event. The condition being monitored can include an air passageway gap, air flow pressure, and/or wall tension. The deformable element and the sensor element can be in two separate units. Preferably, the sensor element provides feedback to modulate the opening of the air passageway by the deformable element. The device can further include a microprocessor adapted and configured to communicate with the sensor regarding the opening of the air passageway and controlling an energizing of the deformable element based on this communication with the sensor element. The device can also include a non-implanted portion. In some embodiments, the non-implanted portion comprises a battery and in other embodiments it comprises a microprocessor adapted and configured to communicate with the sensor regarding the opening of the air passageway and controlling an energizing of the deformable element based on this communication with the sensor element. The sensor element can be located proximal to or in the nose, nostril, soft palate, tongue, laryngeal wall, and/or a pharyngeal wall. The sensor element can be a non-contact distance sensor, pressure sensor, flow sensor, and/or a wall tension sensor.

Another aspect of the invention is methods of use of the airway implant device which include a sensor. One embodiment is a method of treating a disease using an airway implant device comprising implanting a deformable element proximal to and/or in a wall of an air passageway, wherein the deformable element is adapted and configured to monitor a condition of the air passageway to determine likelihood of an apneic event and to modulate an opening of the air passageway based on the monitoring. Another embodiment is a method of treating a disease using an airway implant device comprising implanting a deformable element and a sensor element proximal to and/or in a wall of an air passageway, wherein the deformable element is adapted and configured to modulate an opening of an air passageway and the sensor is adapted and configured to monitor a condition of the air passageway to determine likelihood of an apneic event. The sensor element can be further adapted and configured to provide a feedback to the deformable element regarding the condition being monitored and the modulation by the deformable element is related to the feedback. The sensor element can also activate the deformable element, the activation being related to the monitoring by the sensor element. Diseases suitable for treatment with the devices include obstructive sleep apnea and/or snoring. Yet another embodiment is a method of treating a disease using an airway implant device comprising implanting a deformable element and a sensor element proximal to and/or in a wall of an air passageway; the deformable element being adapted and configured to control an opening of an air passageway by energizing the deformable element, wherein the energizing of the deformable element moves the soft palate to support a collapsed tongue and completely or partially opens the air passageway or supports the lateral pharyngeal wall and completely or partially opens up the air passageway and the energizing is in response to feedback from the sensor element regarding an opening of the air passageway.

In one embodiment, the present invention provides an airway implant device having a deformable element and a tether element, wherein the deformable element is adapted and configured to modulate an opening of an air passageway and the tether element is adapted and configured to fasten the deformable element to a bony structure.

In one aspect, the deformable element includes a magnetic material or an electroactive polymer element.

In another aspect, the deformable element and the tether element include a polymeric material, wherein the polymeric material of the deformable element is an electroactive polymer.

In another aspect, the deformable element includes an electroactive polymer element. The electroactive polymer element can include an ion-exchange polymer metal composite, or a conducting polymer. The conducting polymer can include a polypyrrole, a carbon nanotube or a polyaniline. The implant having an electroactive polymer element can also include a power supply in electrical communication with the electroactive polymer element, and where the application of electrical current to the electroactive polymer element opens an air passageway. The implant having an electroactive polymer element can also include a n inductive coupling mechanism adapted to connect the electroactive polymer element to a power source.

In another aspect, the deformable electroactive polymer element includes an anode, a cathode, a first inductor, and a controller; the anode and cathode being connected to the deformable element. The controller can have a microprocessor, and the microprocessor is adapted and configured to sense an opening of the air passageway and configured for controlling an energizing of the deformable element.

In another aspect, the implant also includes a non-implanted portion. The non-implanted portion can be in the shape of a strip, where the strip is adapted and configured to control said deformable element. The strip can also include a power supply and a second inductor, where the second inductor is adapted and configured to interact with a first inductor connected with the implantable portion.

In another aspect, the deformable element is adapted and configured for implantation into a tongue.

In another aspect, the deformable element includes a flat surface or a tube, or a structure that is adapted and configured to expand and contract like an accordion.

The airway implant device can also include a coating to prevent tissue growth.

In another aspect, the airway implant device can also include to promote tissue growth.

In another aspect, the airway implant device can also include a sensor element, wherein the sensor is adapted and configured to monitor a condition of an airway to determine likelihood of an apneic event. The condition being monitored can be an air passageway gap, air flow pressure, and/or wall tension. The sensor can provide feedback to modulate the opening of the air passageway by the deformable element.

In another embodiment, the present invention provides a method of treating a disease using an airway implant device. The method includes implanting in a subject an airway implant device having a deformable element and a tether element, the implanting step including fastening the deformable element to a bony structure of the subject with the tether element, wherein the deformable element is adapted and configured to modulate an opening of an air passageway.

In another embodiment, the present invention provides a method of treating a disease using an airway implant device. The method includes implanting a deformable element in a tongue of a subject and tethering the deformable element to a jaw bone, the deformable element being adapted and configured to support the tongue upon being energized. The airway disease can be a sleeping disorder, and the sleeping disorder can be obstructive sleep apnea or snoring.

In another embodiment, the present invention provides an implant for stabilizing the tongue. The implant includes a first anchoring portion for securing a first end of the implant with the mandibula; a control portion connected with the anchoring portion, configured for selectively activating the implant; a flexible portion connected at its proximal end with the control portion, the flexible portion having three-dimensional flexibility in a first state and the flexible portion having a lesser three-dimensional flexibility in a second state, said flexible portion being selectively switchable between the first and second state by the control portion; and a second anchoring portion connected with the distal end of the flexible portion, the second anchoring portion being configured for connecting the implant with the base of the tongue.

In one aspect, the first anchoring portion includes an anchoring bracket.

In another aspect, the control portion includes a spring-biased linear motor coupled with a flexible fiber, the fiber connected at its proximal end with a load movable by the motor and the fiber connected at its distal end with the second anchoring portion, the flexible fiber being configured to impart an axial load on the flexible portion.

In another aspect, the control portion is powered by a non-implanted inductively coupled power source.

In another aspect, the control portion includes a shape memory alloy.

In another aspect, the control portion includes an electro active polymer.

In another aspect, the flexible portion includes a flexible helical spring.

In another aspect, the flexible portion includes a bellows structure.

In another aspect, the flexible portion includes an etched stent-like portion.

In another aspect, the flexible portion is coated with a hyaluronic acid coating.

In another aspect, the second anchoring portion includes a first disc connected with the distal end of the flexible portion and a second disc connectible with the base of the tongue. The first and second discs have suture holes disposed around their circumferences. The first and second discs can include polyester rods having holes extending from their surfaces.

For a further understanding of the nature and advantages of the invention, reference should be made to the following description taken in conjunction with the accompanying figures. It is to be expressly understood, however, that each of the figures is provided for the purpose of illustration and description only and is not intended as a definition of the limits of the embodiments of the present invention.

BRIEF DESCRIPTION OF THE DRAWINGS

FIG. 9 illustrates an embodiment of the electroactive polymer element.

FIG. 10 illustrates an embodiment of the electroactive polymer element.

FIG. 11 illustrates an embodiment of the electroactive polymer element.

FIG. 12 illustrates an embodiment of the electroactive polymer element.

FIG. 13 illustrates an embodiment of the electroactive polymer element.

FIG. 14 illustrates an embodiment of the electroactive polymer element.

FIG. 15 illustrates an embodiment of the electroactive polymer element.

FIG. 16 illustrates an embodiment of the electroactive polymer element.

DETAILED DESCRIPTION OF THE INVENTION

Devices and Methods

Figure 1:
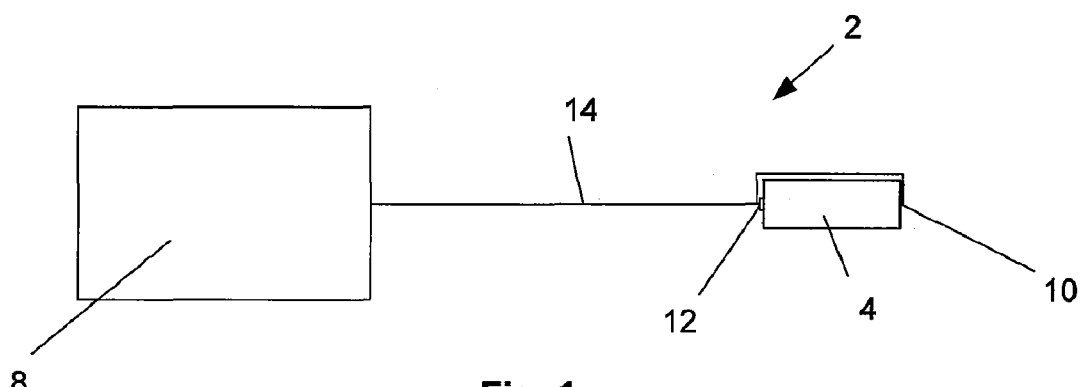
FIG. 1 illustrates one embodiment of the airway implant device.

A first aspect of the invention is a device for the treatment of disorders associated with improper airway patency, such as snoring or sleep apnea. The device comprises of a deformable element to adjust the opening of the airway. In a preferred embodiment, the deformable element comprises of an electroactive polymer (EAP) element. The electroactive polymer element in the device assists in maintaining appropriate airway opening to treat the disorders. Typically, the EAP element provides support for the walls of an airway, when the walls collapse, and thus, completely or partially opens the airway.

The device functions by maintaining energized and non-energized configurations of the EAP element. In preferred embodiments, during sleep, the EAP element is energized with electricity to change its shape and thus modify the opening of the airway. Typically, in the non-energized configuration the EAP element is soft and in the energized configuration is stiffer. The EAP element of the device can have a pre-set non-energized configuration wherein it is substantially similar to the geometry of the patient's airway where the device is implanted.

In some embodiments, the device, in addition to the EAP element, includes an implantable transducer in electrical communication with the EAP element. A conductive lead connects the EAP element and the implantable transducer to the each other. The device of the present invention typically includes a power supply in electrical communication with the EAP element and/or the implantable transducer, such as a battery or a capacitor. The battery can be disposable or rechargeable.

Preferred embodiments of the invention include a non-implanted portion, such as a mouthpiece, to control the implanted EAP element. The mouthpiece is typically in conductive or inductive communication with an implantable transducer. In one embodiment, the mouthpiece is a dental retainer with an induction coil and a power source. The dental retainer can further comprise a pulse-width-modulation circuit. When a dental retainer is used it is preferably custom fit for the individual biological subject. If the implantable transducer is in inductive communication, it will typically include an inductive receiver, such as a coil. The implantable transducer can also include a conductive receiver, such as a dental filling, a dental implant, an implant in the oral cavity, an implant in the head or neck region. In one embodiment, the device includes a dermal patch with a coil, circuit and power source, in communication with the implantable transducer. The dermal patch can also include a pulse-width-modulation circuit.

Another aspect of the invention is a method to modulate air flow through airway passages. Such modulation is used in the treatment of diseases such as snoring and sleep apnea. One method of the invention is a method for modulating the airflow in airway passages by implanting in a patient a device comprising a deformable element and controlling the device by energizing the deformable element. The deformable element preferably comprises an electroactive polymer element. The deformable element can be controlled with a mouthpiece inserted into the mouth of the patient. The energizing is typically performed with the use of a power supply in electrical communication, either inductive communication or conductive communication, with the deformable element. A transducer can be used to energize the deformable element by placing it in electrical communication with the power supply. Depending on the condition being treated, the deformable element is placed in different locations such as soft palate, airway sidewall, uvula, pharynx wall, trachea wall, larynx wall, and/or nasal passage wall.

A preferred embodiment of the device of the present invention comprises an implantable deformable element; an implantable transducer; an implantable lead wire connecting the deformable element and the transducer; a removable transducer; and a removable power source; and wherein the deformable element comprises an electroactive polymer.

Electroactive polymer is a type of polymer that responds to electrical stimulation by physical deformation, change in tensile properties, and/or change in hardness. There are several types of electroactive polymers like dielectric electrostrictive polymer, ion exchange polymer and ion exchange polymer metal composite (IPMC). The particular type of EAP used in the making of the disclosed device can be any of the aforementioned electroactive polymers.

Suitable materials for the electroactive polymer element include, but are not limited to, an ion exchange polymer, an ion exchange polymer metal composite, an ionomer base material. In some embodiments, the electroactive polymer is perfluorinated polymer such as polytetrafluoroethylene, polyfluorosulfonic acid, perfluorosulfonate, and polyvinylidene fluoride. Other suitable polymers include polyethylene, polypropylene, polystyrene, polyaniline, polyacrylonitrile, cellophane, cellulose, regenerated cellulose, cellulose acetate, polysulfone, polyurethane, polyvinyl alcohol, polyvinyl acetate, polyvinyl pyrrolidone. Typically, the electroactive polymer element includes a biocompatible conductive material such as platinum, gold, silver, palladium, copper, and/or carbon.

Suitable shapes of the electroactive polymer element include three dimensional shape, substantially rectangular, substantially triangular, substantially round, substantially trapezoidal, a flat strip, a rod, a cylindrical tube, an arch with uniform thickness or varying thickness, a shape with slots that are perpendicular to the axis, slots that are parallel to the longitudinal axis, a coil, perforations, and/or slots.

IPMC is a polymer and metal composite that uses an ionomer as the base material. Ionomers are types of polymers that allow for ion movement through the membrane. There are several ionomers available in the market and some of the suited ionomers for this application are polyethylene, polystyrene, polytetrafluoroethylene, polyvinylidene fluoride, polyfluorosulfonic acid based membranes like NAFION® (from E. I. Du Pont de Nemours and Company, Wilmington, Del.), polyaniline, polyacrylonitrile, cellulose, cellulose acetates, regenerated cellulose, polysulfone, polyurethane, or combinations thereof. A conductive metal, for example gold, silver, platinum, palladium, copper, carbon, or combinations thereof, can be deposited on the ionomer to make the IPMC. The IPMC element can be formed into many shapes, for example, a strip, rod, cylindrical tube, rectangular piece, triangular piece, trapezoidal shape, arch shapes, coil shapes, or combinations thereof. The IPMC element can have perforations or slots cut in them to allow tissue in growth.

The electroactive polymer element has, in some embodiments, multiple layers of the electroactive polymer with or without an insulation layer separating the layers of the electroactive polymer. Suitable insulation layers include, but are not limited to, silicone, polyurethane, polyimide, nylon, polyester, polymethylmethacrylate, polyethylmethacrylate, neoprene, styrene butadiene styrene, or polyvinyl acetate.

In some embodiments, the deformable element, the entire device, or portions of the airway implant have a coating. The coating isolates the coated device from the body fluids and/or tissue either physically or electrically. The device can be coated to minimize tissue growth or promote tissue growth. Suitable coatings include poly-L-lysine, poly-D-lysine, polyethylene glycol, polypropylene, polyvinyl alcohol, polyvinylidene fluoride, polyvinyl acetate, hyaluronic acid, and/or methylmethacrylate.

Embodiments of the Device

FIG. 1 illustrates an airway implant system 2 that has a power supply 4, a connecting element, such as a wire lead 14, and a deformable element, such as an electroactive polymer element 8. Suitable power supplies 4 are a power cell, a battery, a capacitor, a substantially infinite bus (e.g., a wall outlet leading to a power generator), a generator (e.g., a portable generator, a solar generator, an internal combustion generator), or combinations thereof. The power supply 4 typically has a power output of from about 1 mA to about 5 A, for example about 500 mA.

Instead of or in addition to wire lead 14, the connecting element may be an inductive energy transfer system, a conductive energy transfer system, a chemical energy transfer system, an acoustic or otherwise vibratory energy transfer system, a nerve or nerve pathway, other biological tissue, or combinations thereof. The connecting element is made from one or more conductive materials, such as copper. The connecting element is completely or partially insulated and/or protected by an insulator, for example polytetrafluoroethylene (PTFE). The insulator can be biocompatible. The power supply 4 is typically in electrical communication with the deformable element 8 through the connecting element. The connecting element is attached to an anode 10 and a cathode 12 on the power supply 4. The connecting elements can be made from one or more sub-elements.

The deformable element 8 is preferably made from an electroactive polymer. Most preferably, the electroactive polymer is an ion exchange polymer metal composite (IPMC). The IPMC has a base polymer embedded, or otherwise appropriately mixed, with a metal. The IPMC base polymer is preferably perfluoronated polymer, polytetrafluoroethylene, polyfluorosulfonic acid, perfluorosulfonate, polyvinylidene fluoride, hydrophilic polyvinylidene fluoride, polyethylene, polypropylene, polystyrene, polyaniline, polyacrylonitrile, cellophane, cellulose, regenerated cellulose, cellulose acetate, polysulfone, polyurethane, polyvinyl alcohol, polyvinyl acetate and polyvinyl pyrrolidone, or combinations thereof. The IPMC metal can be platinum, gold, silver, palladium, copper, carbon, or combinations thereof.

Figure 2:
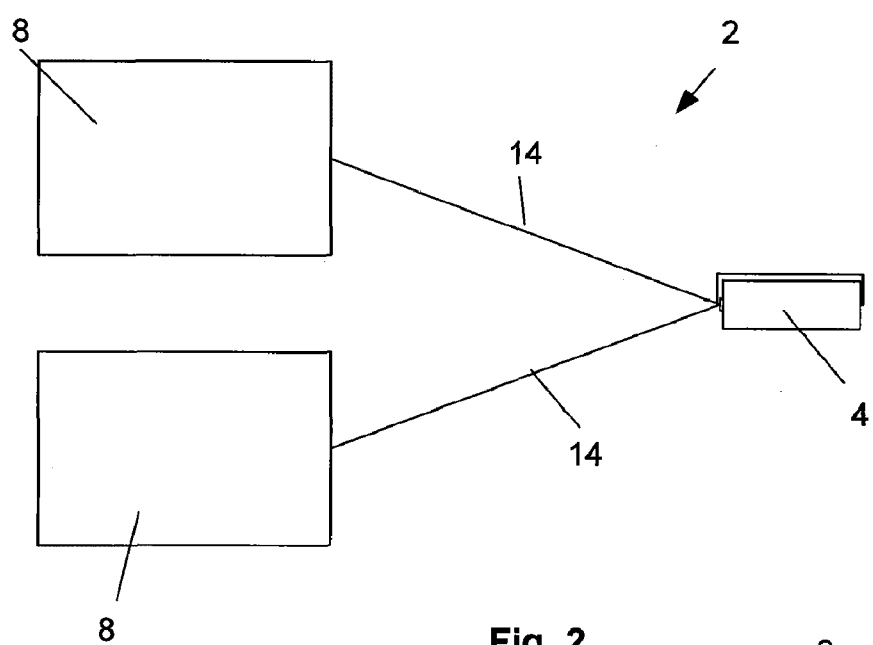
FIG. 2 illustrates one embodiment of the airway implant device.

FIG. 2 illustrates that the deformable element 8 can have multiple elements 8 and connecting elements 14 that all connect to a single power supply 4.

Figure 3:
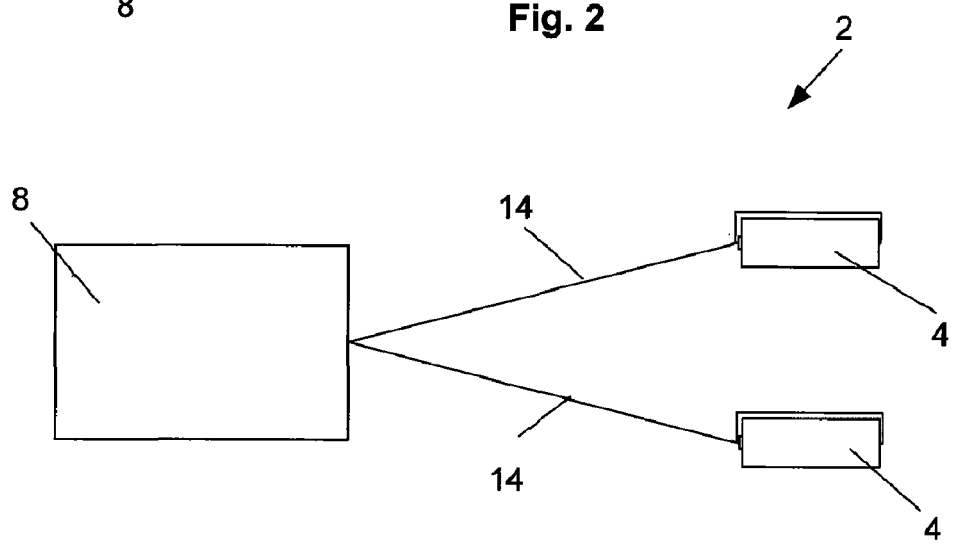
FIG. 3 illustrates one embodiment of the airway implant device.

FIG. 3 illustrates an airway implant system 2 with multiple power supplies 4 and connecting elements 14 that all connect to a single deformable element 8. The airway implant system 2 can have any number and combination of deformable elements 8 connected to power supplies 4.

Figure 4:
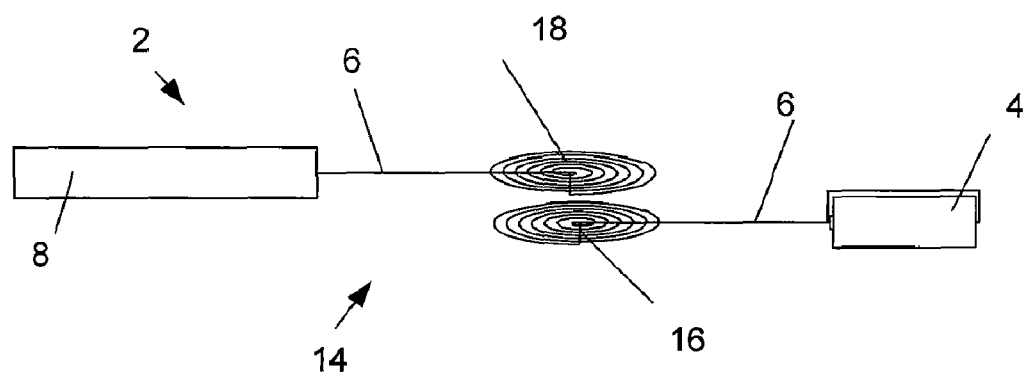
FIG. 4 illustrates one embodiment of the airway implant device.

FIG. 4 illustrates an embodiment with the connecting element having a first energy transfer element, for example a first transducer such as a first receiver, and a second energy transfer element, for example a second transducer such as a second inductor 16. In this embodiment, the first receiver is a first inductor 18. The first inductor 18 is typically positioned close enough to the second inductor 16 to enable sufficient inductive electricity transfer between the second and first inductors 16 and 18 to energize the deformable element 8. The connecting element 14 has multiple connecting elements 6.

Figure 5:
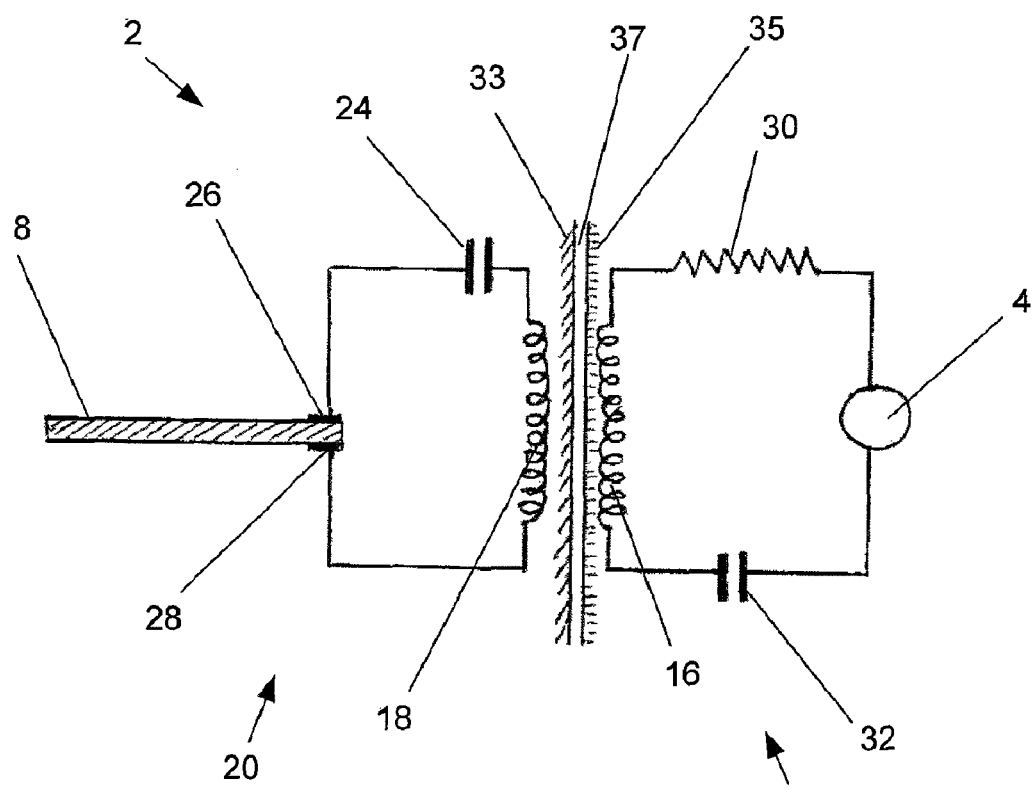
FIG. 5 illustrates a circuit diagram of an embodiment of the airway implant device.

FIG. 5 illustrates that the airway implant device of the present invention can have an implanted portion 20 and a non-implanted portion 22. In this embodiment, the implanted portion 20 is a closed circuit with the first inductor 18 in series with a first capacitor 24 and the deformable element 8. The deformable element 8 is attached to the closed circuit of the implanted portion 20 by a first contact 26 and a second contact 28. In some embodiments, the implanted portion has a resistor (not shown). The non-implanted portion 22 is a closed circuit. The non-implanted portion 22 has a second inductor 16 that is in series with a resistor 30, the power supply 4, and a second capacitor 32. The capacitors, resistors, and, in-part, the inductors are representative of the electrical characteristics of the wire of the circuit and not necessarily representative of specific elements. The implanted portion 20 is within tissue and has a tissue surface 33 nearby. The non-implanted portion is in an insulation material 35. An air interface 37 is between the tissue surface 33 and the insulation material 35.

Figure 6:
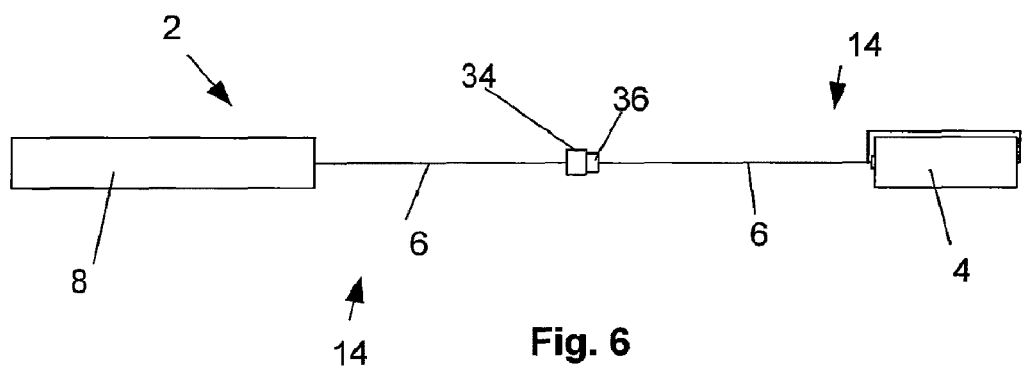
FIG. 6 illustrates an embodiment of the airway implant device.

FIG. 6 illustrates an embodiment in which the first energy transfer element of the connecting element 14 is a first conductor 34. The second energy transfer element of the connecting element 14 is a second conductor 36. The first conductor 34 is configured to plug into, receive, or otherwise make secure electrical conductive contact with the second conductor 36. The first conductor 34 and/or second conductor 36 are plugs, sockets, conductive dental fillings, tooth caps, fake teeth, or any combination thereof.

Figure 7:
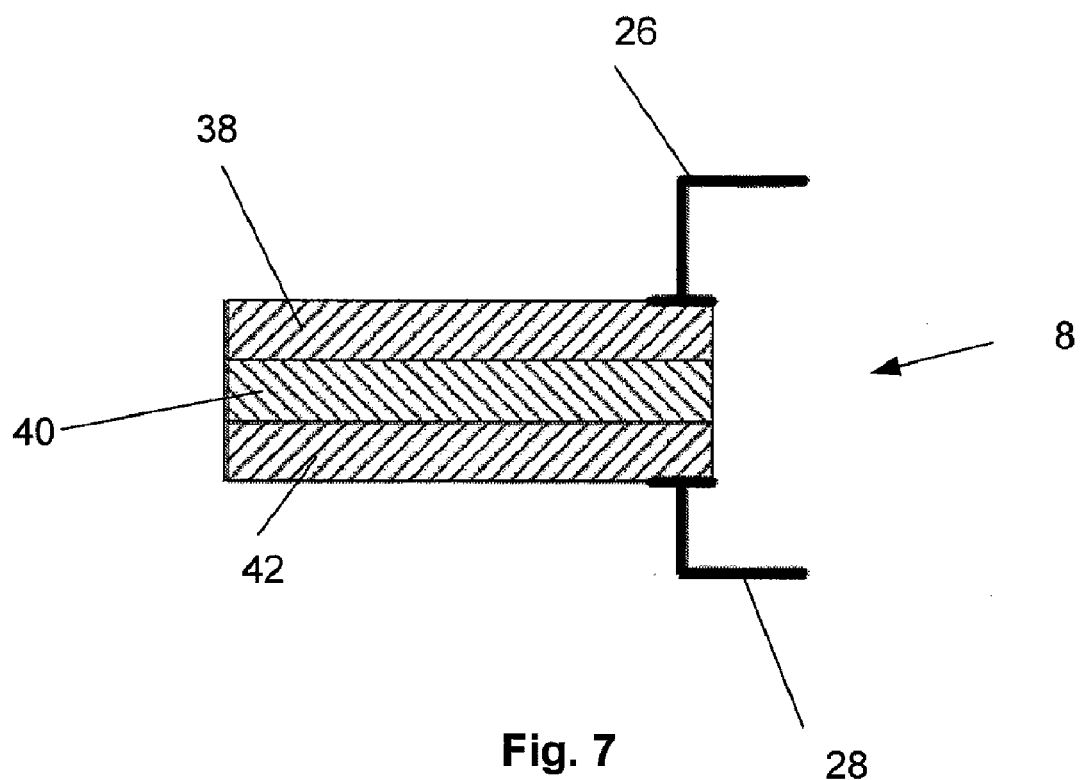
FIG. 7 illustrates a sectional view of an embodiment of the electroactive polymer element.

FIG. 7 illustrates an embodiment in which the deformable element 8 is a multi-layered device. The deformable element 8 has a first EAP layer 38, a second EAP layer 40, and a third EAP layer 42. The EAP layers 38, 40 and 42 are in contact with each other and not separated by an insulator.

Figure 8:
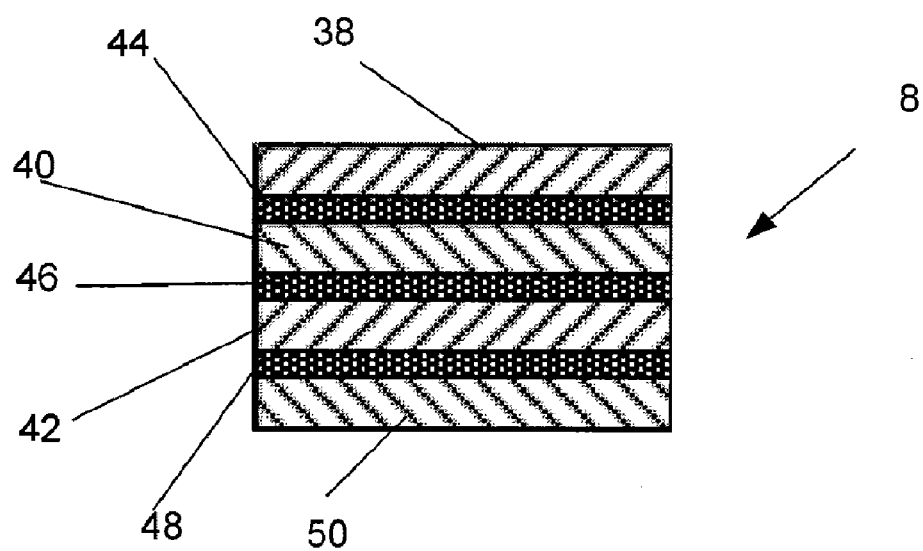
FIG. 8 illustrates a sectional view of an embodiment of the electroactive polymer element.

FIG. 8 illustrates another embodiment in which the deformable element 8 has a first EAP layer 38 separated from a second EAP layer 40 by a first insulation layer 44. A second insulation layer 46 separates the second EAP layer from the third EAP layer 42. A third insulation layer 48 separates the third EAP layer from the fourth EAP layer 50. Insulation material is preferably a polymeric material that electrically isolates each layer. The insulation can be, for example, acrylic polymers, polyimide, polypropylene, polyethylene, silicones, nylons, polyesters, polyurethanes, or combinations thereof. Each EAP layer, 38, 40, 42 and 50 can be connected to a lead wire (not shown). All anodes and all cathodes are connected to the power supply 4.

Figure 17:
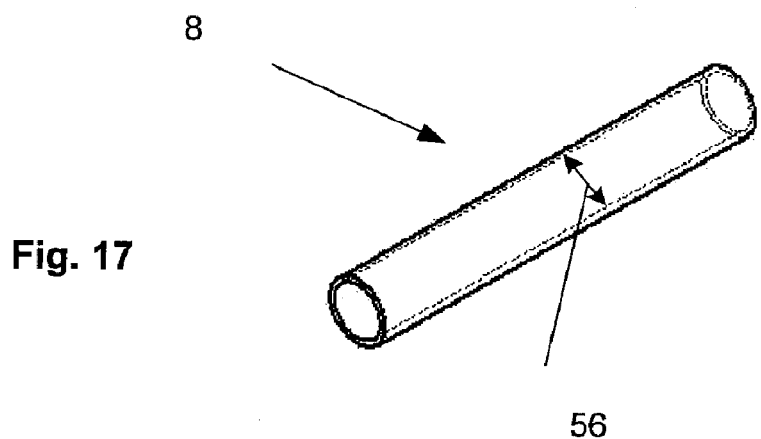
FIG. 17 illustrates an embodiment of the electroactive polymer element.
Figure 18:
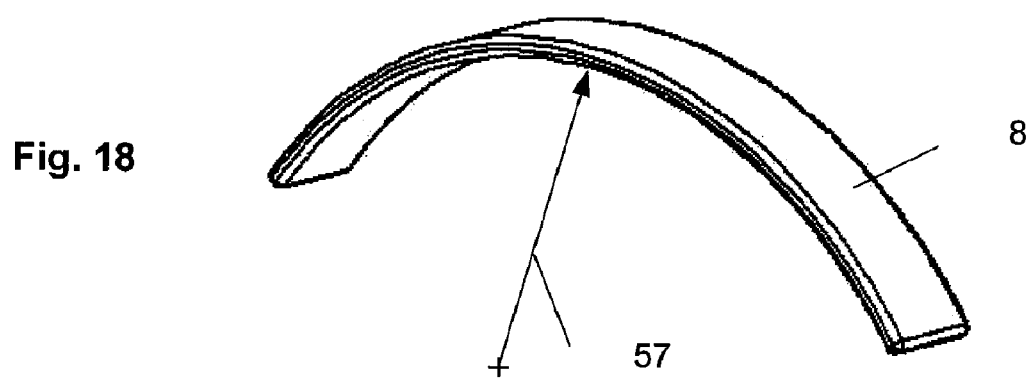
FIG. 18 illustrates an embodiment of the electroactive polymer element.
Figure 19:
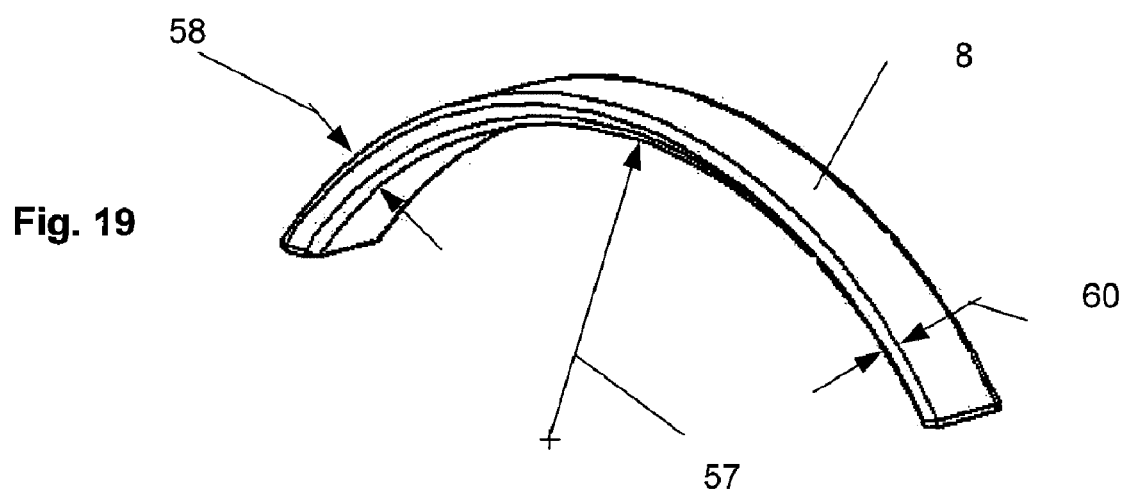
FIG. 19 illustrates an embodiment of the electroactive polymer element.

FIGS. 9-19 illustrate different suitable shapes for the deformable element 8. FIG. 9 illustrates a deformable element 8 with a substantially flat rectangular configuration. The deformable element 8 can have a width from about 2 mm to about 5 cm, for example about 1 cm. FIG. 10 illustrates a deformable element 8 with an "S" or zig-zag shape. FIG. 11 illustrates the deformable element 8 with an oval shape. FIG. 12 illustrates a deformable element 8 with a substantially flat rectangular shape with slots 52 cut perpendicular to the longitudinal axis of the deformable element 8. The slots 52 originate near the longitudinal axis of the deformable element 8. The deformable element 8 has legs 54 extending away from the longitudinal axis. FIG. 13 illustrates a deformable element 8 with slots 52 and legs 54 parallel with the longitudinal axis. FIG. 14 illustrates a deformable element be configured as a quadrilateral, such as a trapezoid. The deformable element 8 has chamfered corners, as shown by radius. FIG. 15 illustrates a deformable element 8 with apertures 55, holes, perforations, or combinations thereof FIG. 16 illustrates a deformable element 8 with slots 52 and legs 54 extending from a side of the deformable element 8 perpendicular to the longitudinal axis. FIG. 17 illustrates a deformable element 8 with a hollow cylinder, tube, or rod. The deformable element has an inner diameter 56. FIG. 18 illustrates an arched deformable element 8. The arch has a radius of curvature 57 from about 1 cm to about 10 cm, for example about 4 cm. The deformable element 8 has a uniform thickness. FIG. 19 illustrates an arched deformable element 8. The deformable element 8 can have a varying thickness. A first thickness 58 is equal or greater than a second thickness 60.

Figure 20:
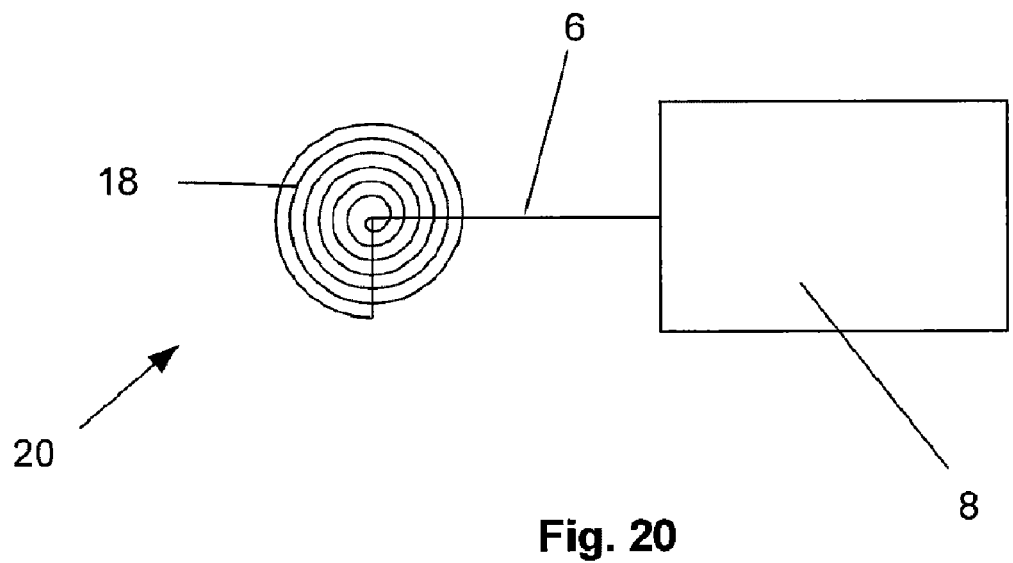
FIG. 20 illustrates an embodiment of the implanted portion of the airway implant device.
Figure 21:
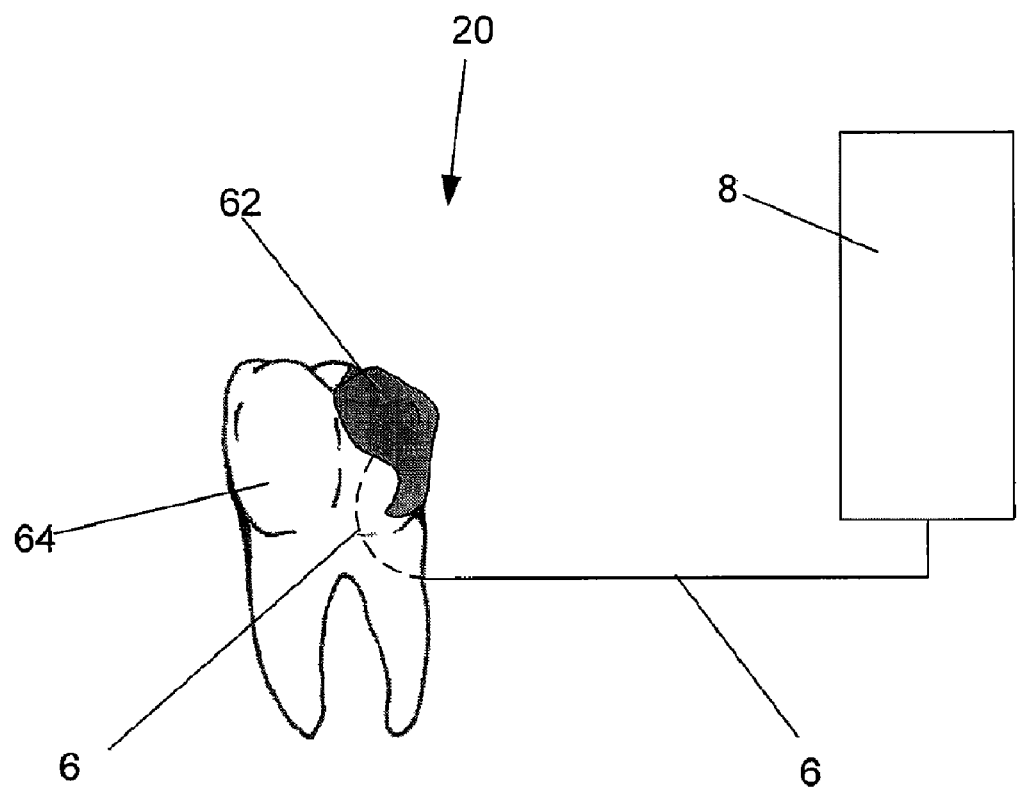
FIG. 21 illustrates an embodiment of the airway implant device.

FIG. 20 illustrates an embodiment of the implanted portion of an airway implant with a coil-type inductor 18 connected by a wire lead 6 to the deformable element 8. In another embodiment, as illustrated in FIG. 21 the implanted portion has a conductive dental filling 62 in a tooth 64. The dental filling 62 is previously implanted for reasons related or unrelated to using of the airway implant system. The dental filling 62 is electrically connected to the wire lead 6. For example, a portion of the wire lead 6 is implanted in the tooth 64, as shown by phantom line. The wire lead 6 is connected to the deformable element 8.

Figure 22:
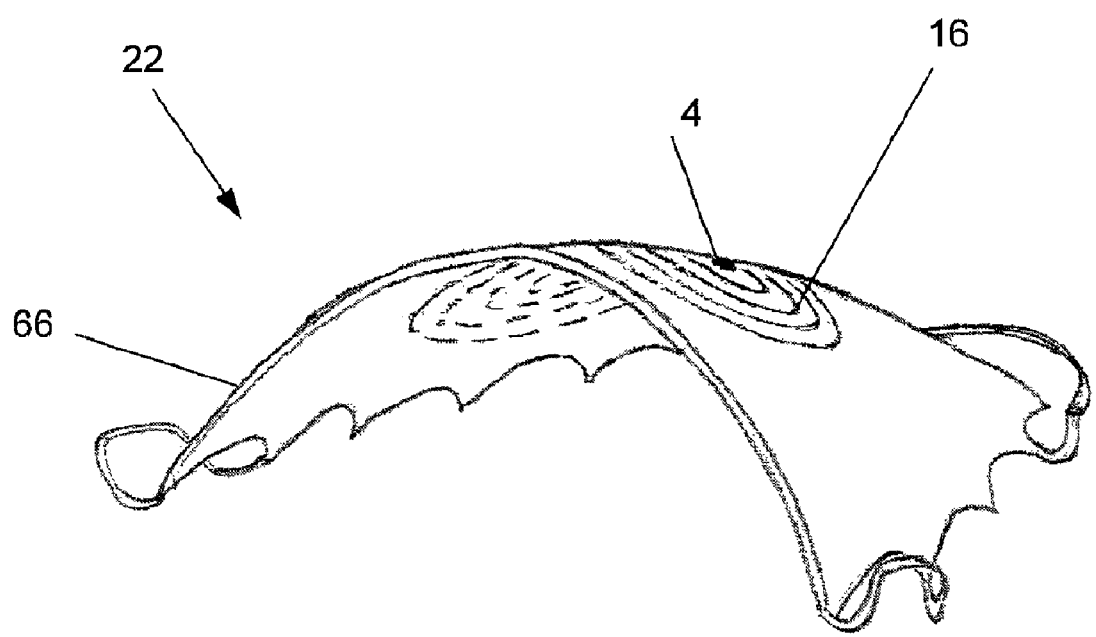
FIG. 22 illustrates an embodiment of the non-implanted portion in the form of a mouth guard.
Figure 23:
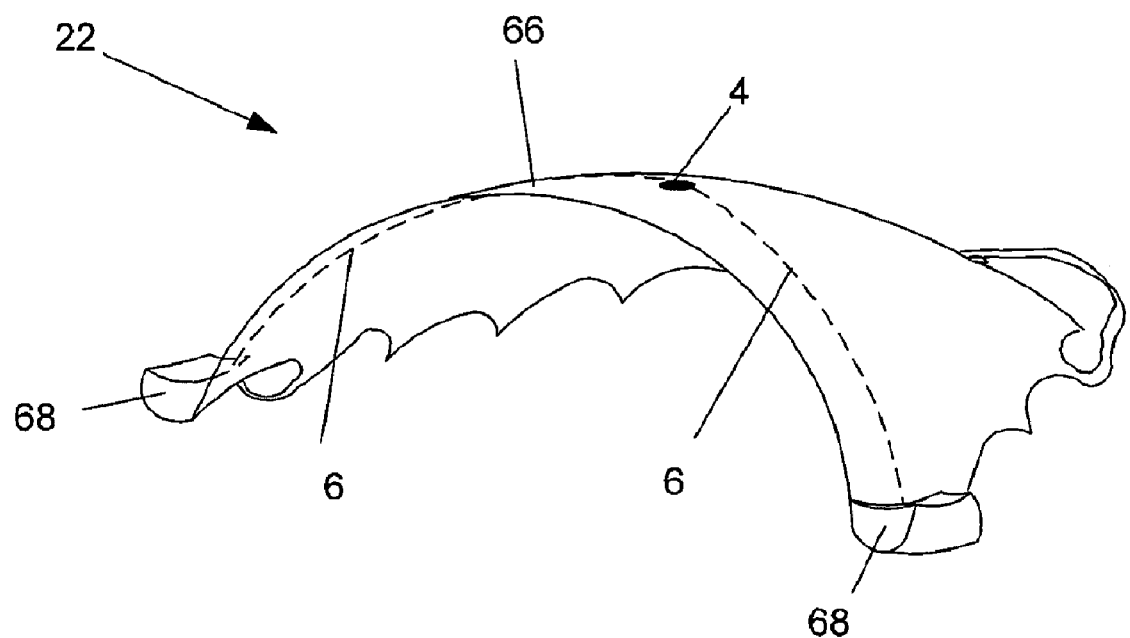
FIG. 23 illustrates an embodiment of the non-implanted portion in the form of a mouth guard.
Figure 24:
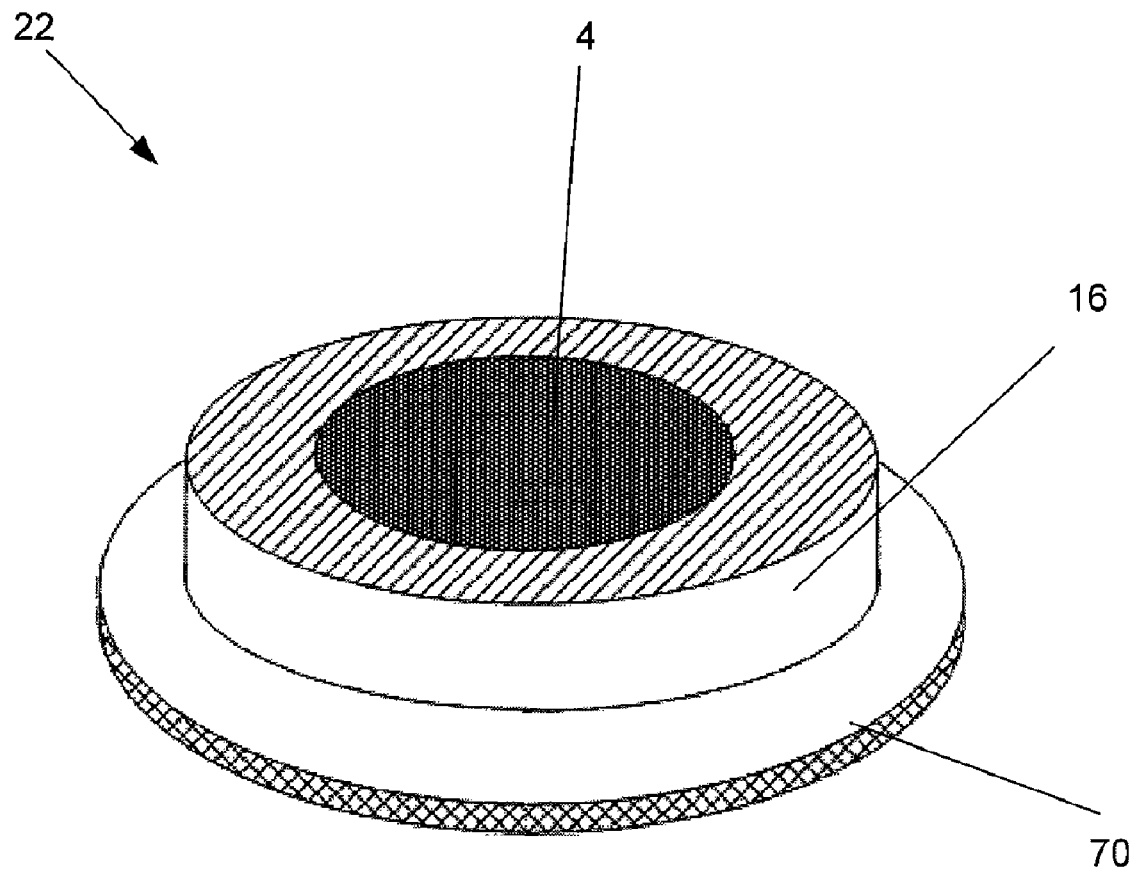
FIG. 24 illustrates an embodiment of the non-implanted portion.

FIG. 22 illustrates an embodiment of the non-implanted portion 22 with a mouthpiece, such as a retainer 66. The retainer 66 is preferably custom configured to fit to the patient's mouth roof, or another part of the patient's mouth. The second transducer, such as second inductor 16, is integral with, or attached to, the retainer 66. The second inductor 16 is located in the retainer 66 so that during use the second inductor 16 is proximal with the first inductor 18. The power supply 4, such as a cell, is integral with, or attached to, the retainer 66. The power supply 4 is in electrical communication with the second inductor 16. In some embodiments, the retainer 66 has a pulse-width-modulation circuit. FIG. 23 illustrates that the retainer 66 has one or more tooth sockets 68. The tooth sockets 68 are preferably configured to receive teeth that have dental fillings. The tooth sockets 68 are electrically conductive in areas where they align with dental fillings when in use. The power supply 4 is connected with the tooth sockets 68 via the wire leads 6. In the embodiment of FIG. 24, the non-implantable portion 22 has the second inductor 16 attached to a removably attachable patch 70. The patch 70 is attached to the power supply 4. The power supply 4 is in contact with the second inductor 16. This embodiment can be, for example, located on the cheeks as shown on FIG. 33 or any other suitable location.

Figure 30:
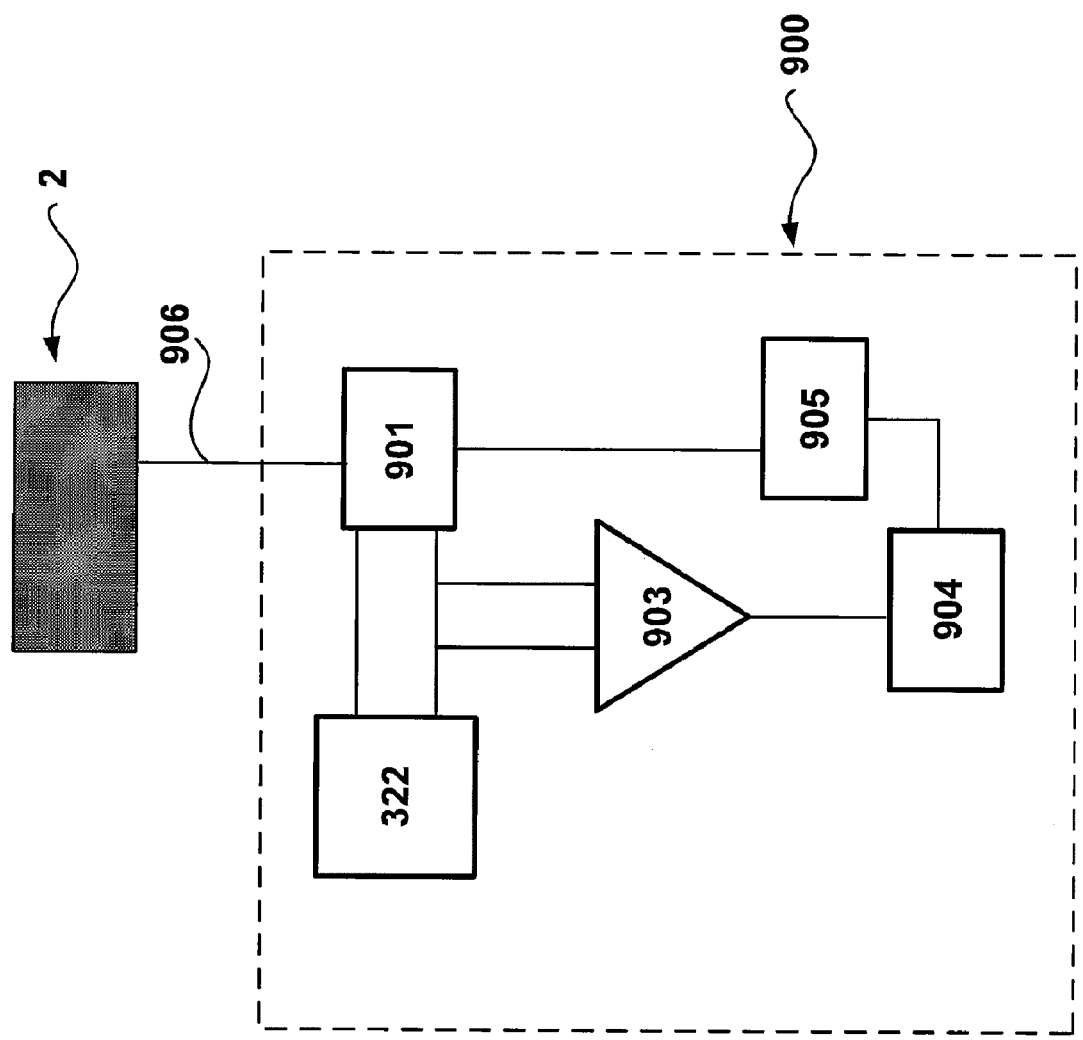
FIG. 30 illustrates an embodiment of an inductive coupling system associated with the airway implant device.

Preferably, the airway implant device 2 discussed herein is used in combination with an inductive coupling system 900 such as depicted in FIG. 30. FIG. 30 depicts an inductive coupling system that is suitable for controlling the airway implant device 2 which includes a connecting element 906 (which connects the electrical contacts (not shown) to the rest of the electrical system), a connector 901, a energy source 322, a sensor 903, a timer 904, and a controller 905. The connector 901, energy source 322, sensor 903, a timer 904, and controller 905 are located in a housing disposed in a region outside or inside the body.

Figure 31:
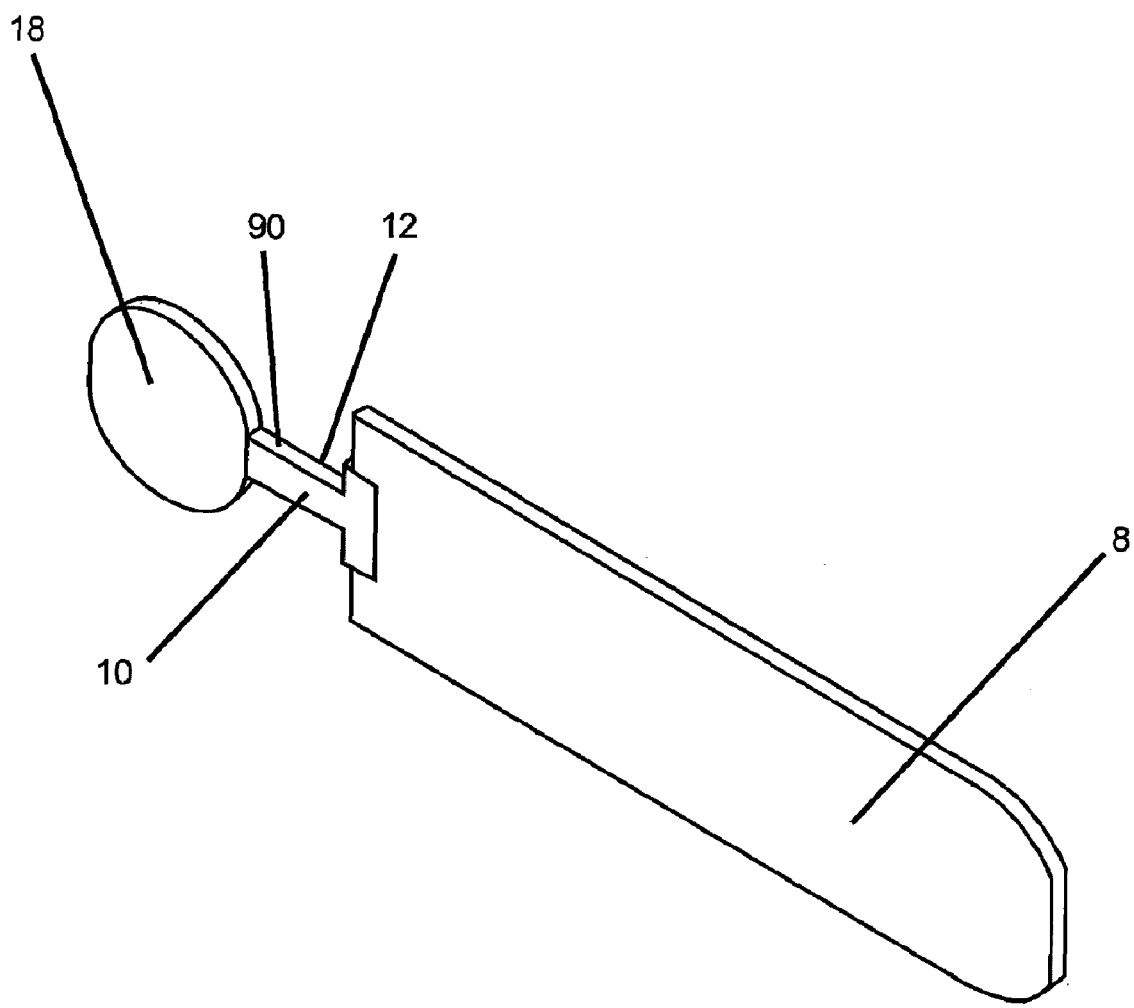
FIG. 31 illustrates an embodiment of the airway implant device.
Figure 32:
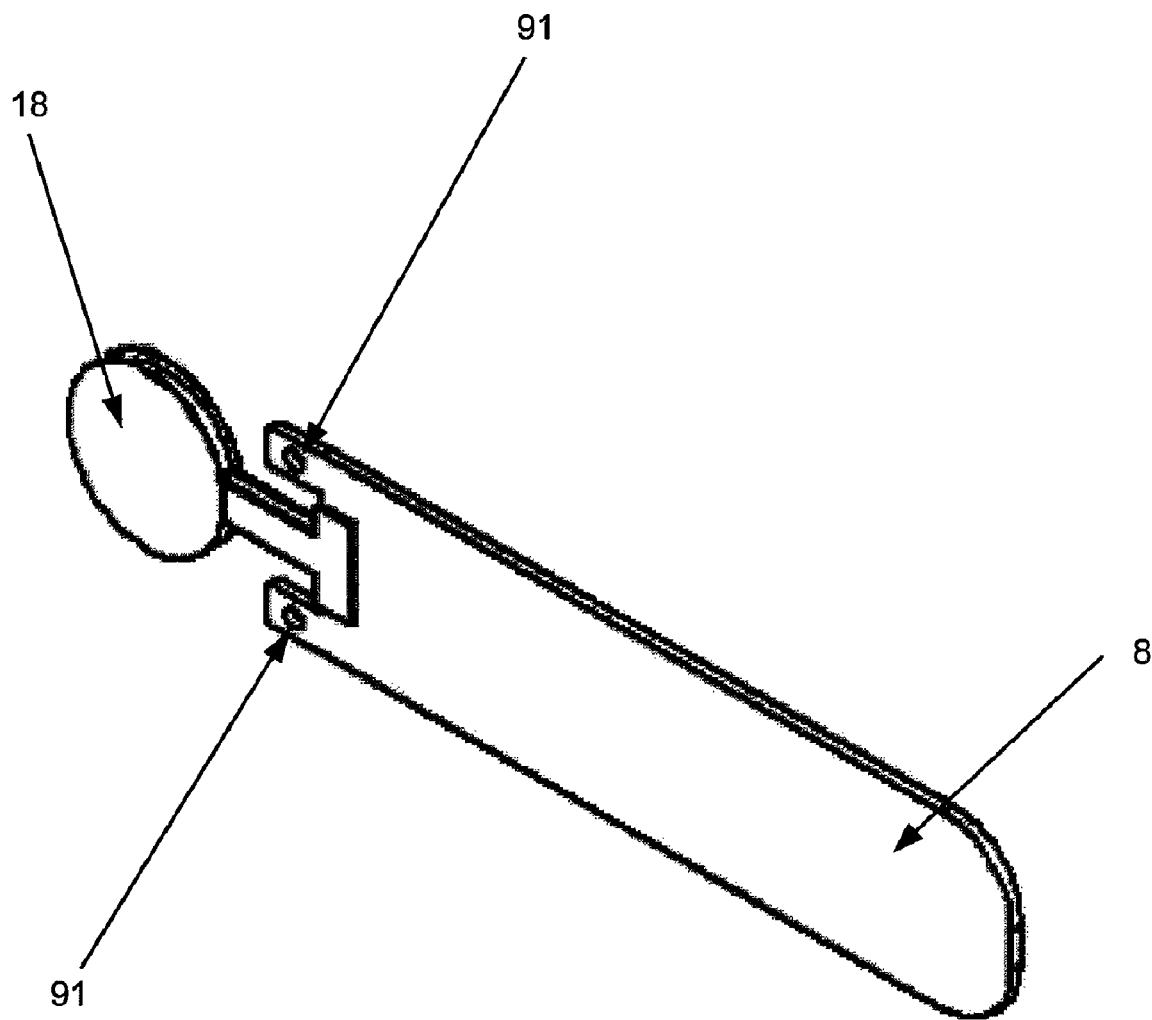
FIG. 32 illustrates an embodiment of the airway implant device.

Two preferred embodiments of the airway implant device are shown in FIGS. 31 and 32. The device in FIG. 31 includes the deformable element 8 connected to an anode 10 and cathode 12 and to the induction coil 18. The device also includes a controller 90, such as a microprocessor. The circuitry within the controller is not shown. The controller 90 picks up AC signals from the induction coil 18 and converts it to DC current. The controller 90 can also include a time delay circuit and/or a sensor. The sensor could sense the collapsing and/or narrowing of the airways and cause the device to energize the deform able element 8 and thus completely or partially open up the airway in which the device is implanted. FIG. 32 shows an embodiment with anchors 91 located on the deformable element 8. The implant can be anchored in a suitable location with the use of these anchors and sutures and/or surgical glue.

Figure 42:
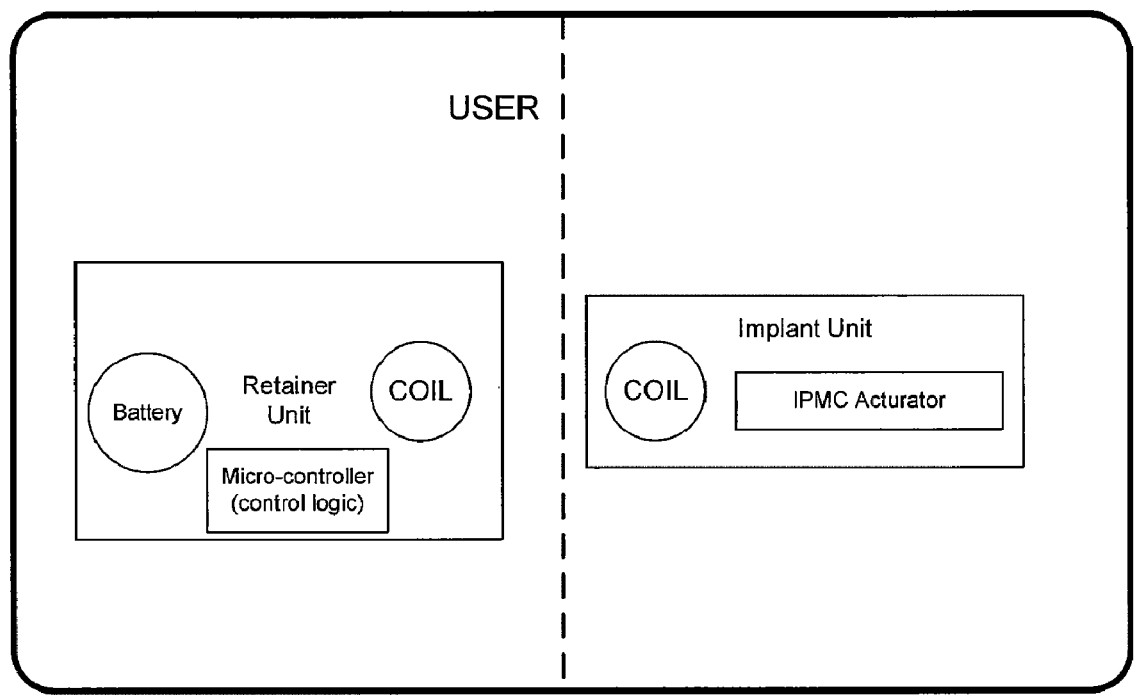
FIG. 42 depicts an embodiment of an airway implant device.

FIG. 42 depicts an embodiment of the invention. The airway implant device comprises of two units—an implant unit and a retainer unit. The implant unit is implanted in a patient and includes an IPMC actuator and a coil. The retainer unit is typically not implanted in the patient and can be worn by the patient prior to going to bed. This unit includes a coil, a battery, and a microcontroller.

Figure 43A:
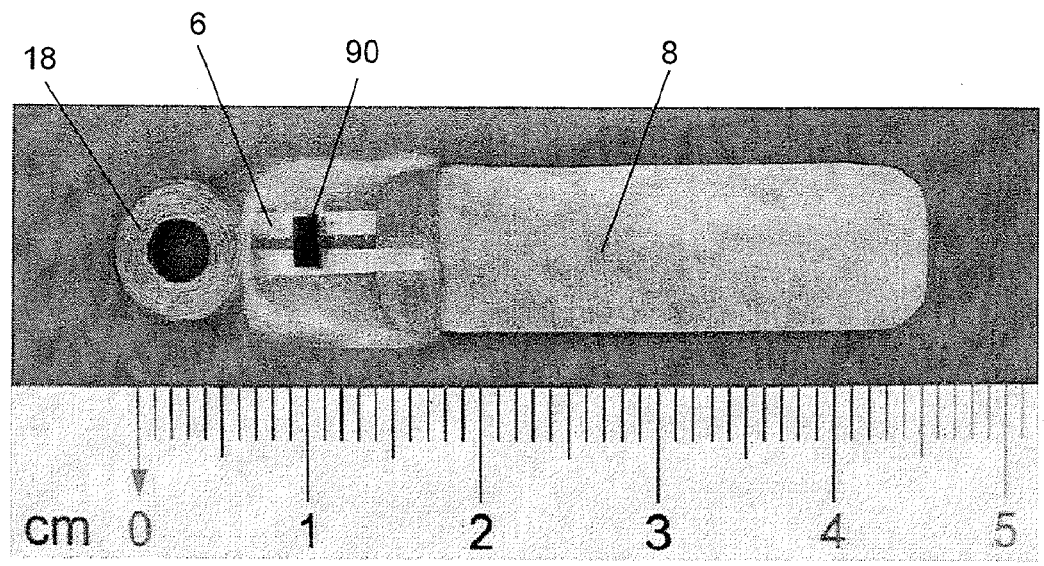
FIG. 43A depicts an embodiment of an airway implant device.
Figure 43B:
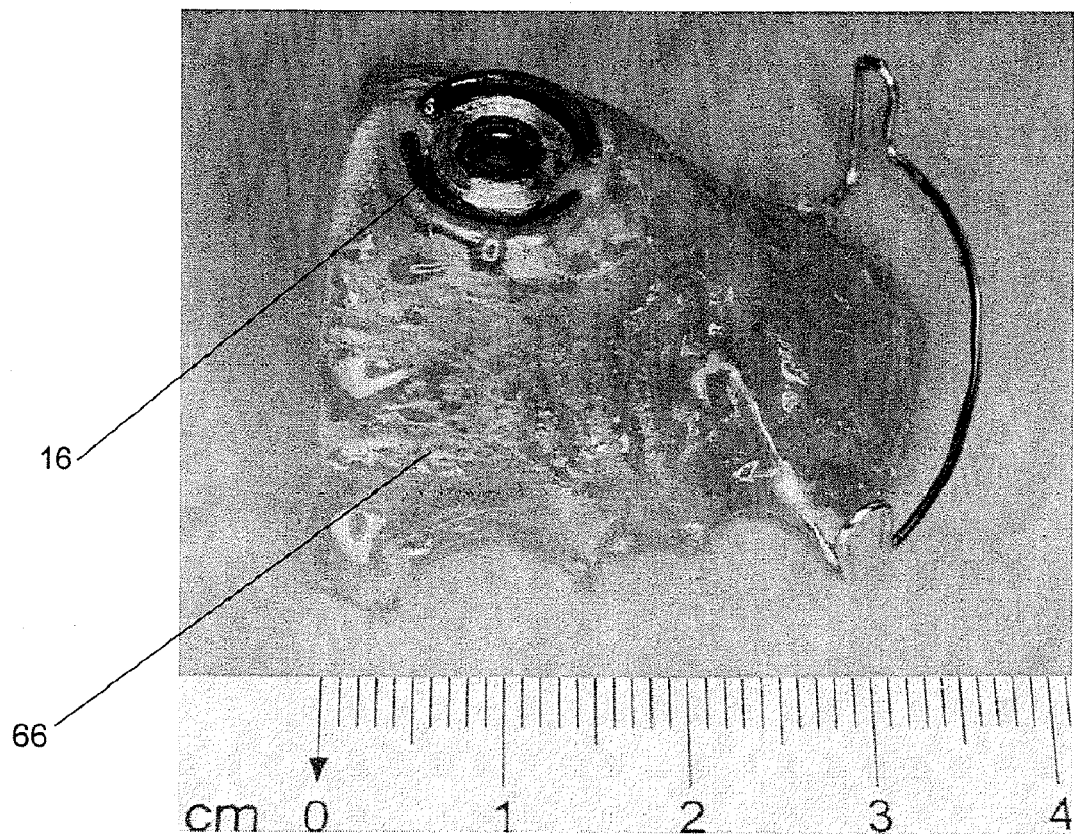
FIG. 43B depicts an embodiment of the non-implantable portion of the airway implant device of FIG. 43A.

FIG. 43A-B depicts yet another embodiment of the invention. FIG. 43A is the implant unit, preferably for implantation proximal to or in an airway wall. The implant unit includes a deformable element 8, an inductor 18 in the form of a coil, a controller 90, and connecting elements 6. FIG. 43B depicts the removable retainer with an inductor 16 and a retainer 66.

The implants described herein are preferably implanted with a deployment tool. Typically, the implantation involves an incision, surgical cavitation, and/or affixing the implant.

Sensing and Actuation of Airway Implants

One embodiment of the invention is an airway implant device with a sensor for monitoring a condition prior to and/or during the occurrence of an apneic event. Preferably, the sensor monitors for blockage of an airway. The sensor senses the possible occurrence of an apneic event. This sensing of a possible apneic event is typically by sensing a decrease in the airway gap, a change in air pressure in the airway, or a change in air flow in the airway. A progressive decrease in the airway gap triggers the occurrence of an apneic event. Most preferably the sensor senses one or more events prior to the occurrence an apneic event and activates the airway implant to prevent the apneic event. In some embodiments, the airway implant device and the sensor are in the same unit. In other embodiments, the deformable element of the airway implant device is the sensor. In these embodiments, the deformable element acts as both a sensor and actuator. In yet other embodiments, the airway implant device and the sensor are in two or more separate units.

Figure 37:
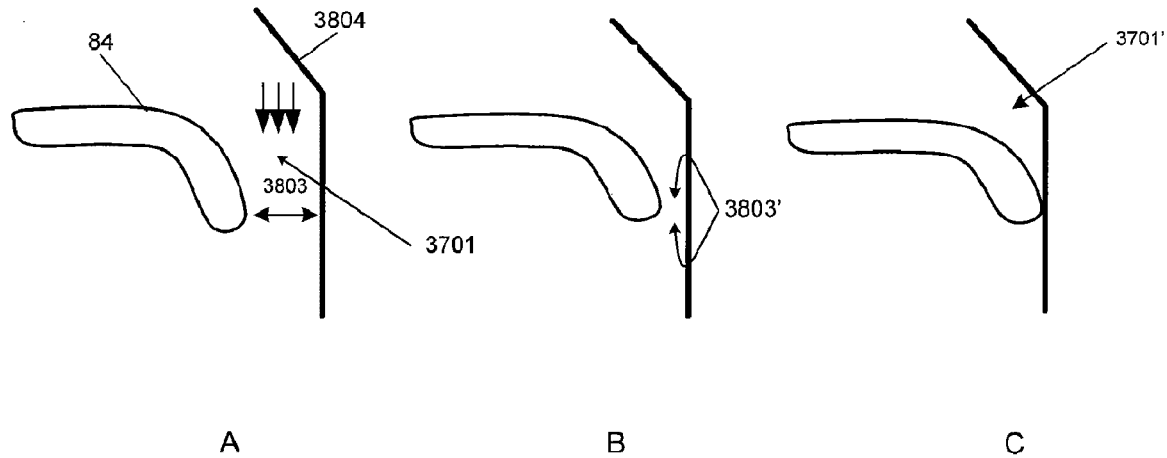
FIG. 37 depicts the progression of an apneic event.

FIG. 37 depicts the occurrence of an apneic event due to the blockage of airway 3701 caused by the movement of the soft palate 84. FIG. 37A shows the soft palate 84 position during normal breathing cycle. An airway gap 3803 is maintained between the soft palate 84 and the laryngeal wall 3804 to maintain airflow 3805. FIG. 37B shows the position of the soft palate 84 just prior to the airway 3701 blockage. It can be seen that the gap 3803' in this case is smaller than the gap 3803 in FIG. 37A. FIG. 37C shows the soft palate 84 blocking the airway 3701', leading to the occurrence of an apneic event. In one aspect of the invention, the event shown in FIG. 37C is prevented by taking preemptive action during occurrence of event depicted in FIG. 37B.

One aspect of the invention is an airway implant device with a sensor for sensing the occurrence of apneic events and actuating the device. The invention also includes methods of use of such device.

Figure 38:
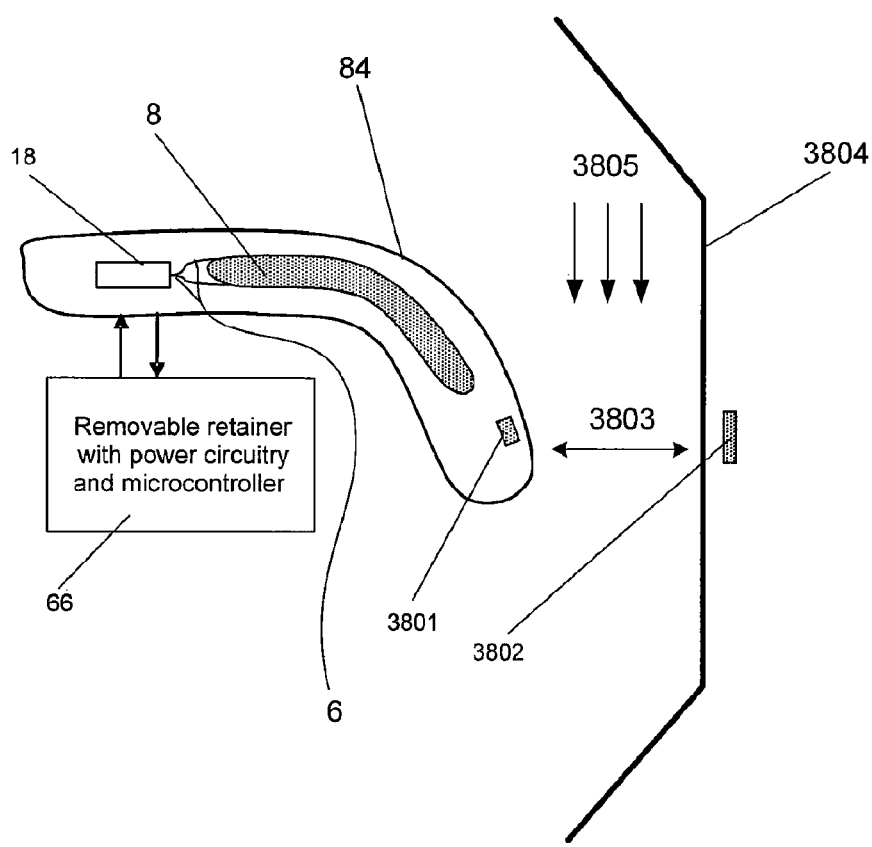
FIG. 38 depicts an embodiment of an airway implant device with sensors in the soft palate and laryngeal wall.
Figure 39:
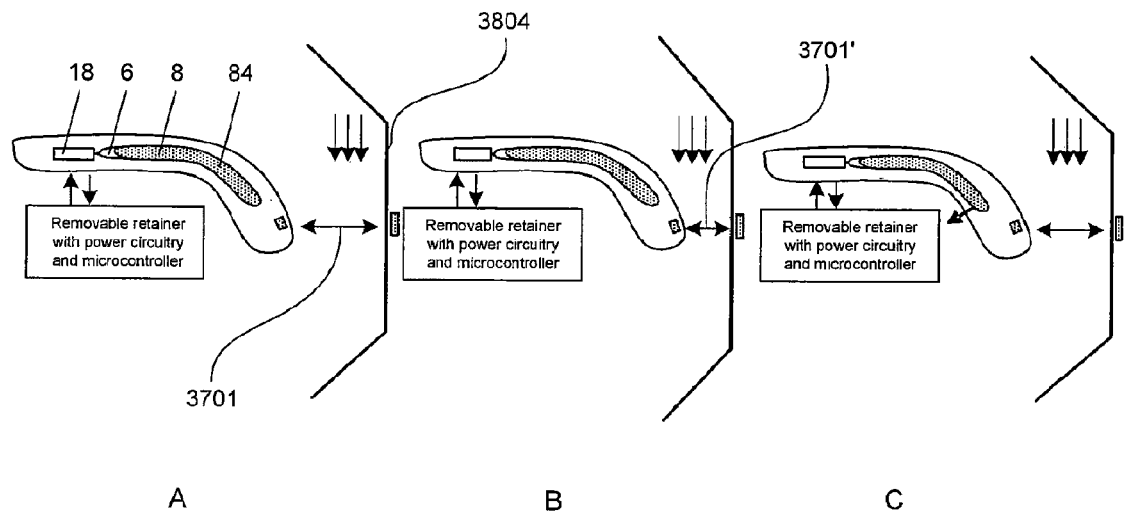
FIG. 39 depicts the functioning of an airway implant device with sensors in the soft palate and laryngeal wall.

One embodiment of an airway implant device with sensor is depicted in FIG. 38. Non-contact distance sensors 3801 and 3802 are mounted on the laryngeal wall 3804 and also on the soft palate 84 to sense the airway gap between the soft palate 84 and the laryngeal wall 3804. One or more gap values are calibrated into a microcontroller controlling the airway implant device. The functioning of the airway implant device with a sensor is depicted in FIG. 39. During the occurrence of the apneic event the gap between the soft palate 84 and the laryngeal wall 3804 decreases. This gap information is continuously monitored by the airway implant device microcontroller. When the gap becomes smaller than a preset threshold value, the airway implant microcontroller actuates the airway implant, which stiffens the soft palate 84 and the gap between the soft palate 84 and the laryngeal walls 3804 increases. When this gap crosses an upper threshold, the microcontroller powers off the airway implant actuator.

In one embodiment, the operation of the device is as follows:

a) A threshold gap is calibrated into the microcontroller which is present in the removable retainer of the device. This threshold gap corresponds to the gap 3803' formed by the position of the soft palate with respect to the laryngeal wall as depicted in the FIG. 37B, i.e., a distance at which an apneic event could be triggered or an apneic event occurs. This calibration can take place in real time or when the device is being installed.

b) The non-contact sensor constantly monitors the gap and the information is constantly analyzed by a program present in the microcontroller.

c) The airway implant actuator is in the off state (not powered state) as long as the threshold gap is not reached.

d) When the gap is equal to the threshold gap, the micro controller, powers on the airway implant actuator (on state). This leads to the stiffening of the airway implant actuator, which in-turn stiffens the soft palate.

e) This stiffening of the soft palate prevents the obstruction of the airway and modulates the occurrence of an apneic event.

f) When the gap becomes more than the threshold gap, the micro-controller turns off the airway implant actuator (off state).

Typically, an algorithm in the micro-controller controls the actuation of the actuator. An example of the algorithm is— if (gap < threshold gap); {Voltage applied to airway implant actuator = high (on state)} or else {Voltage applied to the airway implant actuator = low (off state)}

Complex algorithms, such as adaptive algorithms, can also be used. The objective of the adaptive algorithm can be to selectively control the stiffness of the soft palate by varying the power applied to the airway implant actuator.

Another example of an algorithm to selectively control the stiffness of the soft palate is:

If (gap < or = g)
{Apply full power to the airway implant actuator}
Else
If (gap =g1)
{Voltage applied to airway implant actuator = v1}
Else if (gap = g2)
{Voltage applied to airway implant actuator = v2}
Else if (gap =g3)
{Voltage applied to airway implant actuator =v3}
Note (g1, g2, g3 > g)

Figure 41:
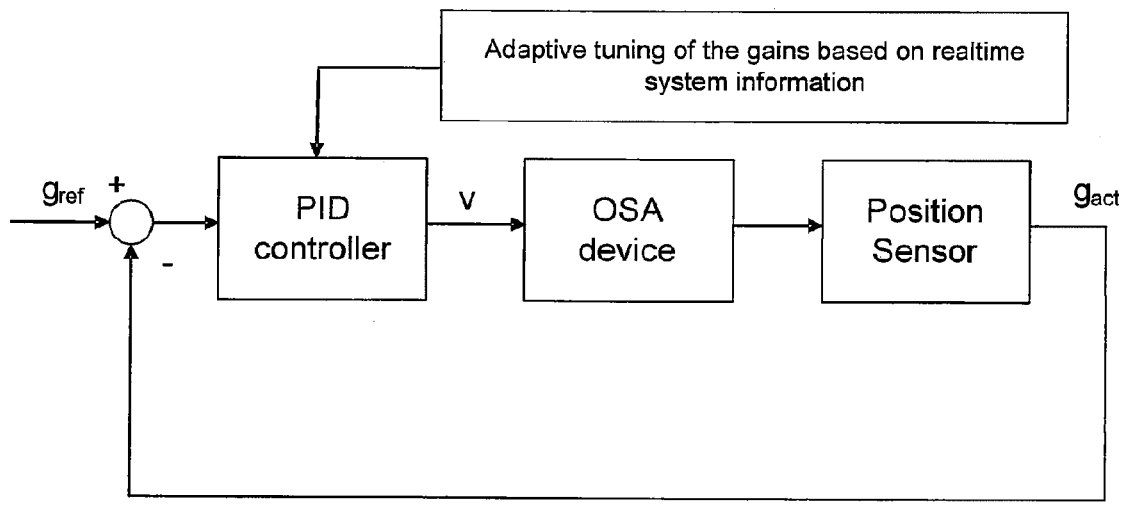
FIG. 41 depicts an example of controller suitable for use with an airway implant device.

An example of a controller to maintain a predetermined reference gap is shown is FIG. 41. The objective of this algorithm is to maintain an actual airway gap $g_{act}$ as close to the reference airway gap $g_{ref}$ as possible by controlling the airway implant device actuator. The actual airway gap between the soft palate and the laryngeal wall $g_{act}$ is measured and this information is the output of the position sensor This airway gap information is feedback to the microcontroller which has a controller algorithm embedded in it. In the microcontroller the $g_{act}$ is compared to a $g_{ref}$ and based on the difference between both, the Proportional Integral Derivative (PID) controller generates a controlling voltage which is supplied to the airway implant device. The PID controller can have fixed gains or can have the gains adaptively tuned based on system information.

In alternative embodiments, the sensor can be a wall tension sensor, an air pressure sensor, or an air flow monitoring sensor. In another embodiment, instead of fully turning the airway implant actuator on or off, the actual value of the airway gap can be used to selectively apply varying voltage to the airway implant actuator, hence selectively varying the stiffness of the soft palate. In yet another embodiment, if the airway implant actuator exhibits a lack of force retention over an extended period of time under DC voltage, a feedback control algorithm may be implemented in the microcontroller, which uses the sensory information provided by the sensors to control the stiffness of the soft palate by maintaining the force developed by the airway implant actuator.

Figure 40:
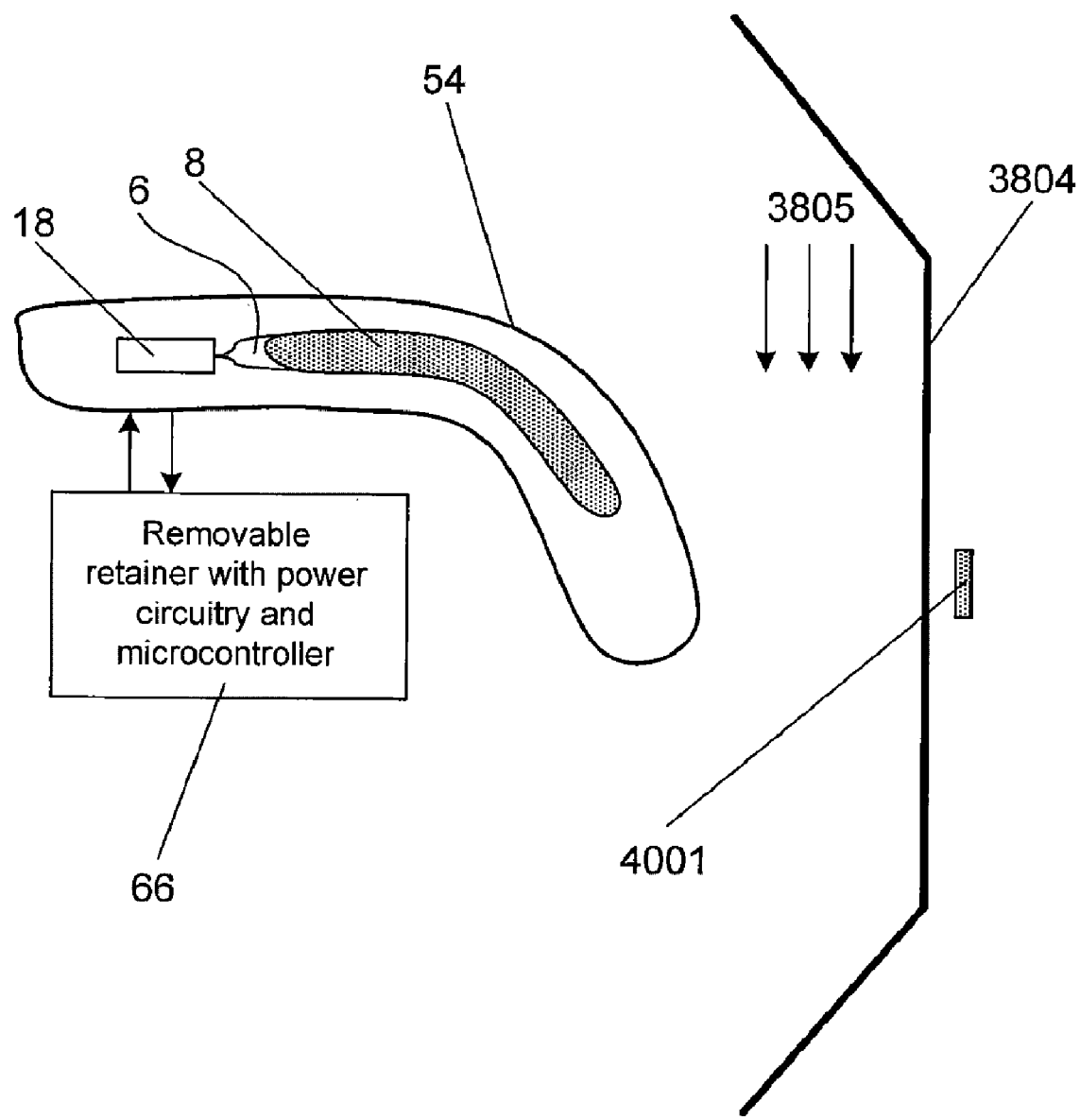
FIG. 40 depicts an embodiment of an airway implant device with a sensor in the laryngeal wall.

Another embodiment of the invention is depicted in FIG. 40. In this embodiment, the wall tension sensed by the wall tension sensor 4001 implanted into the laryngeal wall 3804 is used as a threshold criterion for activating the airway implant actuator. A wall tension sensor can also be placed in a pharyngeal wall or other suitable airway wall. The sensors of this invention can be placed in an airway wall or proximal to an airway wall.

Some of the advantages of the use of an airway sensor with an airway implant device include: optimization of the power consumed by the airway implant device and hence extension of the life of the device; assistance in predicting the occurrence of apneic event, and hence selective activation of the device in order to minimize any patient discomfort; flexibility to use a feedback control system if required to compensate for any actuator irregularities; and possible configuration of the system to interact with an online data management system which will store different parameters related to apneic events for a patient. This system can be accessed by the doctor, other health care providers, and the insurance agency which will help them provide better diagnosis and understanding of the patient's condition.

In preferred embodiments, the airway gap is individually calculated and calibrated for each patient. This information can be stored in the microcontroller. The sensors are described herein mainly in the context of airway implant devices comprising of electroactive polymer actuators. The sensors can also be used with airway implant devices comprising other active actuators, i.e., actuators that can be turned on, off, or otherwise be controlled, such as magnets. The sensors can be used to activate, in-activate, and/or modulate magnets used in airway implant devices. Preferably, the sensors are in the form of a strip, but can be any other suitable shape for implantation. They are typically deployed with a needle with the help of a syringe. The sensor can be made with any suitable material. In preferred embodiments, the sensor is a smart material, such as an IPMC. The sensor is typically in connection with a microcontroller, which is preferably located in the retainer. This connection can be either physical or wireless.

Suitable sensors include, but are not limited to, an electroactive polymer like ionic polymer metal composite (IPMC). Suitable materials for IPMC include perfluorinated polymer such as polytetrafluoroethylene, polyfluorosulfonic acid, perfluorosulfonate, and polyvinylidene fluoride. Other suitable polymers include polyethylene, polypropylene, polystyrene, polyaniline, polyacrylonitrile, cellophane, cellulose, regenerated cellulose, cellulose acetate, polysulfone, polyurethane, polyvinyl acetate. Typically, the electroactive polymer element includes a biocompatible conductive material such as platinum, gold, silver, palladium, copper, and/or carbon. Commercially available materials suitable for use as a sensor include Nafion® (made by DuPont), Flemion® (made by Asahi Glass), Neosepta® (made by Astom Corporation), Ionac® (made by Sybron Chemicals Inc), Excellion™ (made by Electropure). Other materials suitable for use as a sensor include materials with piezoelectric properties like piezoceramics, electrostrictive polymers, conducting polymers, materials which change their resistance in response to applied strain or force (strain gauges) and elastomers.

The airway implant devices of the present invention, with or without the sensor, can be used to treat snoring. For snoring, the sensor can be adapted and configured to monitor air passageways so as to detect the possible occurrence of snoring or to detect the possible worsening of ongoing snoring. Preferably the sensors are capable of detecting relaxation of tissues in the throat, which can cause them to vibrate and obstruct the airway. Other tissues that can be monitored by the sensor include the mouth, the soft palate, the uvula, tonsils, and the tongue.

Another disease that can be treated with the devices of the present invention includes apnea. The sensor preferably monitors the throat tissue for sagging and/or relaxation to prevent the occurrence of an apneic event. Other tissues that can be monitored by the sensor include the mouth, the soft palate, the uvula, tonsils, and the tongue.

Tethered Airway Implant Device

One aspect of the invention is an airway implant device with a tether. Preferably the tether is used to anchor and/or support the airway implant device, in particular, the deformable element to a rigid structure, such as a bony structure. The invention also includes methods of treating a disease using an airway implant device by implanting in a subject the airway implant device having a deformable element and a tether element, the implanting step including fastening the deformable element to a bony structure of the subject with the tether element, wherein the deformable element is capable of modulating the opening of the air passageway. Another method is a method of treating a disease using an airway implant device by implanting a deformable element in a tongue of a subject and tethering the deformable element to a jaw bone, the deformable element is capable of supporting the tongue when it is energized. The devices are used to treat sleeping disorders, such as obstructive sleep apnea or snoring.

One embodiment is an airway implant device having a deformable element and a tether element, wherein the deformable element is capable of modulating the opening of an air passageway and the tether element is used to fasten the deformable element to a rigid structure. Preferably, the rigid structure is a bony structure. The deformable element can be made of a magnetic material or an electroactive polymer element. In some embodiments, both the deformable element and tether element are made from a polymeric material. In this embodiment, the polymeric material of the deformable element is typically an electroactive polymer. The electroactive polymer element can include an ion-exchange polymer metal composite. In other embodiments, the electroactive polymer element can include a conducting polymer such as a polypyrrole, a carbon nanotube or a polyaniline.

Figure 44:
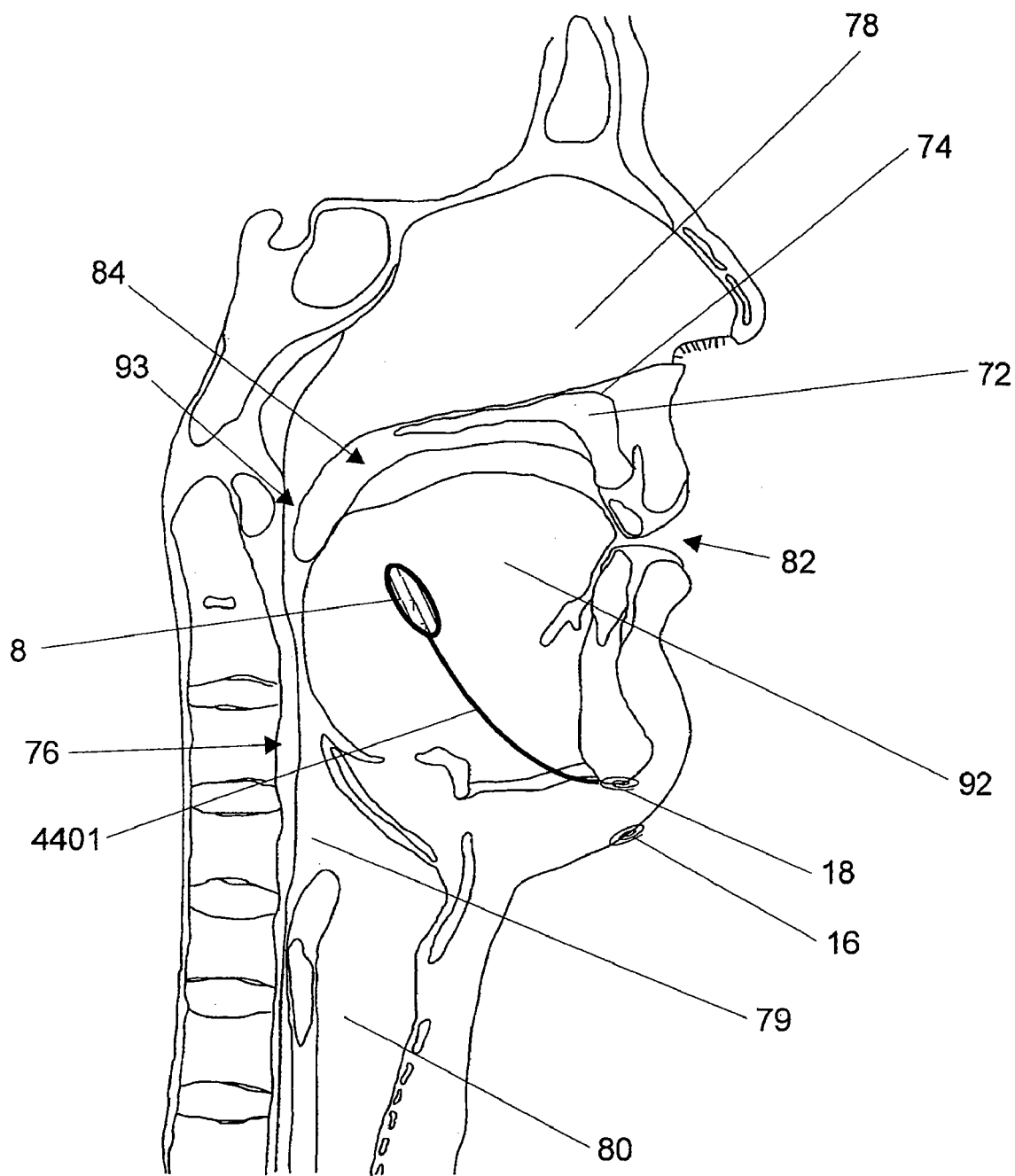
FIG. 44 depicts an embodiment of an airway implant device.

One embodiment of the airway implant device with a tether is depicted in FIG. 44. The deformable element 8 is tethered to the jaw bone with a tether element 4401. A first inductor 18 is implanted in the patient and a second inductor 16 is located on the outside and can be worn by the patient when the airway implant device needs to be activated, for example prior to going to sleep.

Figures 45A, 45B:
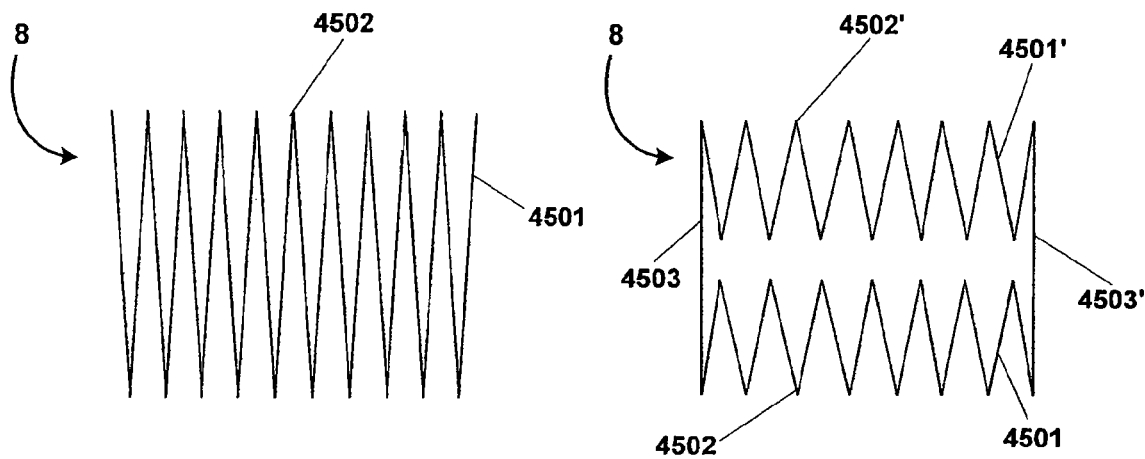
FIG. 45A-D depicts an embodiment of the deformable element.
Figures 45C, 45D:
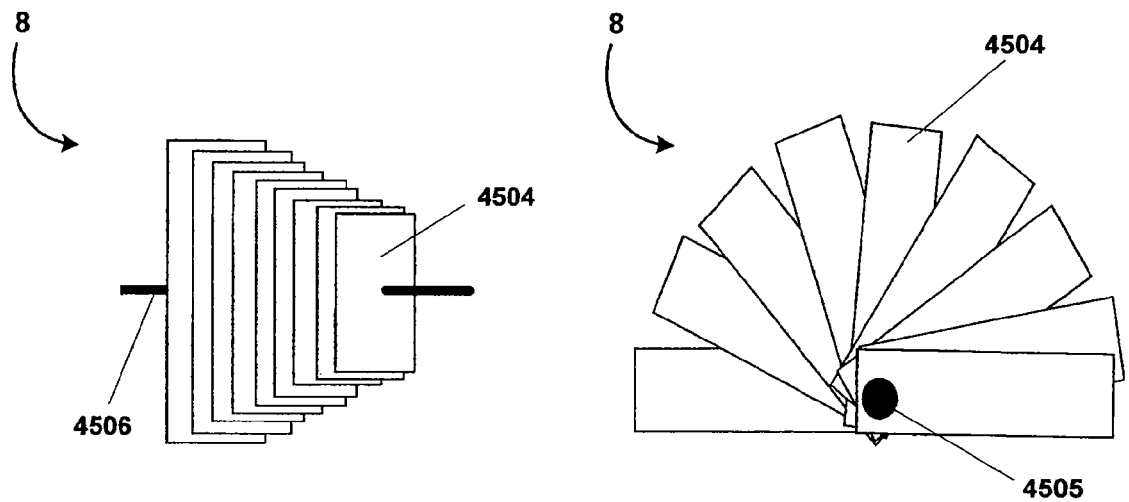

The deformable element can have a suitable shape such as a flat surface or a tube. Preferably, the deformable element is adapted and configured to expand and contract like an accordion, in particular for an airway implant device that is used for implantation in the tongue. Examples of shapes of the deformable element 8 are depicted in FIG. 45A-45D. These forms are particularly useful for implantation in the tongue. FIG. 45A depicts a deformable element 8 with a single layer 4501 of suitable material, such as an electroactive polymer or a magnetic material, with folds 4502. FIG. 45B depicts a deformable element 8 with two layers 4501 and 4501', joined by layers 4503 and 4503' and folds 4502 and 4502'. FIG. 45C depicts a deformable element 8 with a series of layers 4504 which are connected to each other with a connecting element 4506. The connecting element 4506 allows the layers 4504 to slide along its length. The connecting element 4506 and the layers 4504 can be made of the same material or different materials. FIG. 45D depicts a deformable element 8 with a series of layers 4504 which are held together at the connecting point 4505.

In another embodiment, the airway implant device with the tether further includes an anode, a cathode, a first inductor, and a controller. The anode and cathode are typically connected to the deform able element. The controller typically comprises a microprocessor which is capable of sensing the opening of the air passageway and controlling the energizing of the deformable element. The deformable element is energized with a power supply. For example, when the deformable element is an electroactive polymer element, the power supply is in electrical communication with the deformable element and is activated by electrical energy from the power supply. The deformable element can be physically connected to the power supply for example with a wire lead or can be connected with an inductive coupling mechanism.

In an additional embodiment, the airway implant device with the tether further includes a sensor, as described herein. The sensor element is capable of monitoring a condition of an airway to determine likelihood of an apneic event. The condition being monitored is an air passageway gap, air flow pressure, and/or wall tension. The sensor can also provide feedback to modulate the opening of the air passageway by the deformable element.

The airway implant device with a tether further includes in some embodiments a non-implanted portion. Preferably the non-implanted portion is in the form of a strip and is used to control the deformable element. Typically this strip includes a power supply and a second inductor, the second inductor capable of interacting with a first inductor.

The tether element can be used for implanting and/or for retrieving the deformable element, in addition to providing support to the organ being controlled by the airway implant. After implantation, the tether typically extends from deformable element to a rigid structure. The tether can include at one end an additional anchoring feature to assist with the anchoring to the rigid structure. The tether is preferably a wire made of nitinol, stainless steel, titanium or a polymer. The tether can be made from one or polymers, such as, for example, polyester or polyethylene; one or more superelastic metals or alloys, such as, for example, nitinol; or from resorbable synthetic materials, such as, for example suture material or polylactic acid.

As set forth above, certain embodiments of the present invention are related to an implantable device for stabilizing the tongue during sleeping.

Figure 46:
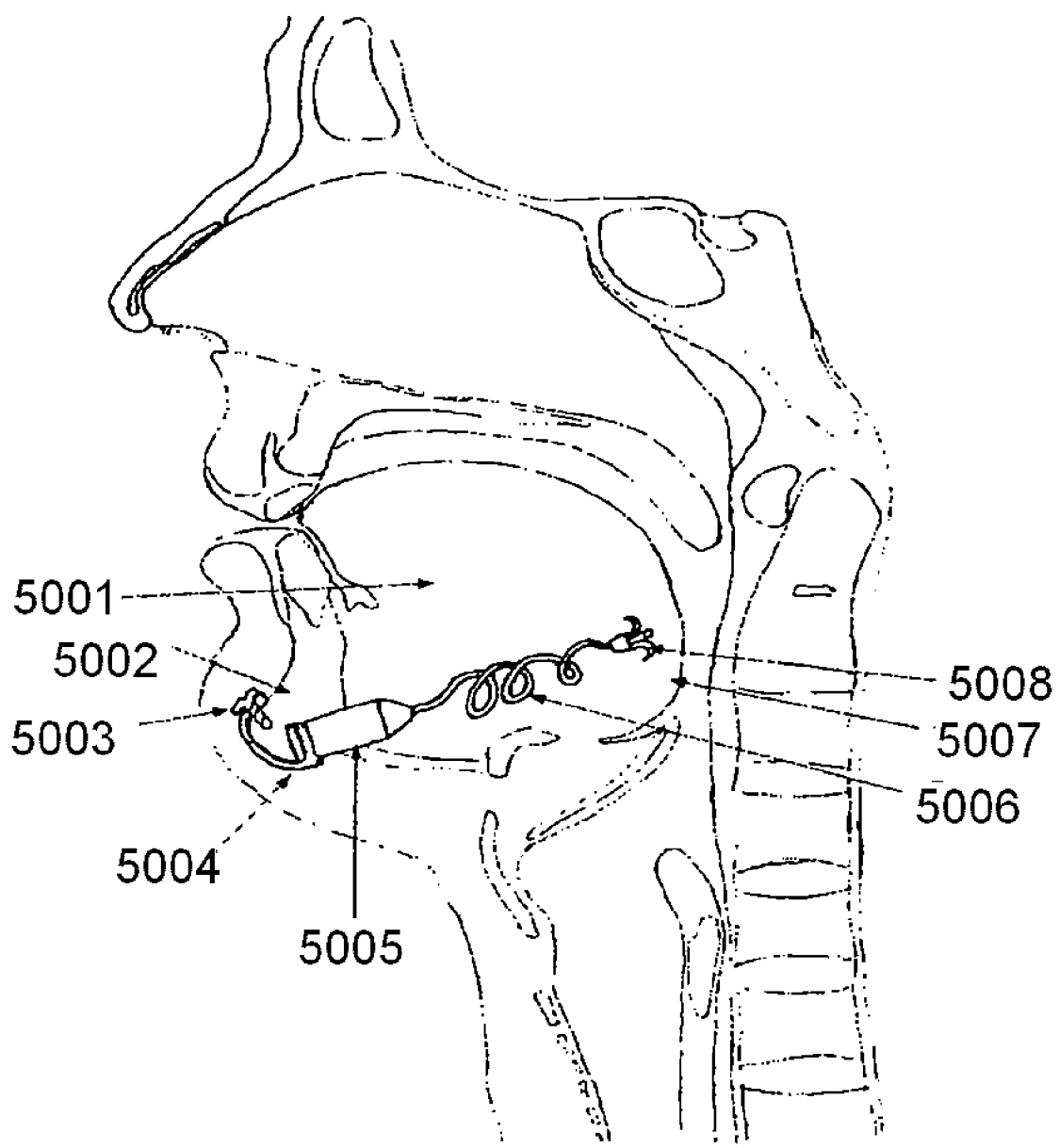
FIG. 46 is a simplified drawing of an exemplary tongue implant device in accordance with one embodiment of the present invention shown implanted in the tongue.

FIG. 46 shows a simplified drawing of an exemplary tongue implant device in accordance with one embodiment of the present invention shown implanted in the tongue. As is shown in FIG. 46, reference number 5001 refers to the tongue; reference number 5002 refers to mandibula; reference number 5003 refers to the anchoring screws; reference number 5004 refers to an anchoring bracket; reference number 5005 refers to the power or actuation module; reference number 5006 refers to a flexible member, which in one embodiment can be a helix-shaped structure; reference number 5007 refers to the base of the tongue; and reference number 5008 refers to the anchor which can be an absorbable anchor.

As is shown in FIG. 46, the tongue implant can have three sections, namely: i) a proximal section that houses the powering mechanism 5005, the actuation mechanism 5005 and the anchoring mechanism 5004 to the patient's mandibula, ii) a middle flexible section 5006 that links the actuation mechanism 5005 to the distal anchor 5008, and iii) a distal anchor 5008, which can be an adsorbable anchor, that allows the implant to be anchored to the base of the tongue 5008. The implant can be placed such that its proximal portion is anchored to the mandibula 5002 and its distal portion is anchored to the base of the tongue 5007.

The Powering/Actuation portion 5005 and its housing can be anchored to the mandibula via a titanium bracket 5004 and titanium bone screws. The actuation mechanisms 5005 can include a Nitinol (actuator type) superelastic shape memory alloys, piezoelectric actuators, and/or electro active polymers, described below in further detail.

The actuator 5005 can be connected to the distal section via a flexible portion 5006 that in one embodiment can be made out of the same actuator material. Alternatively the middle flexible portion 5006 can be made from stainless steel, aramid fiber, polypropylene, nylon or any other suitable material. The flexible portion 5006 can also include a hyaluronic acid (HA) coating to prevent tissue in-growth.

The distal anchor 5008 can be made out of absorbable polymers such as polylactic acid, polyglycolic acid, and so on. Such materials would allow for better integration and anchoring of the implant at the base of the tongue muscle.

Figure 47:
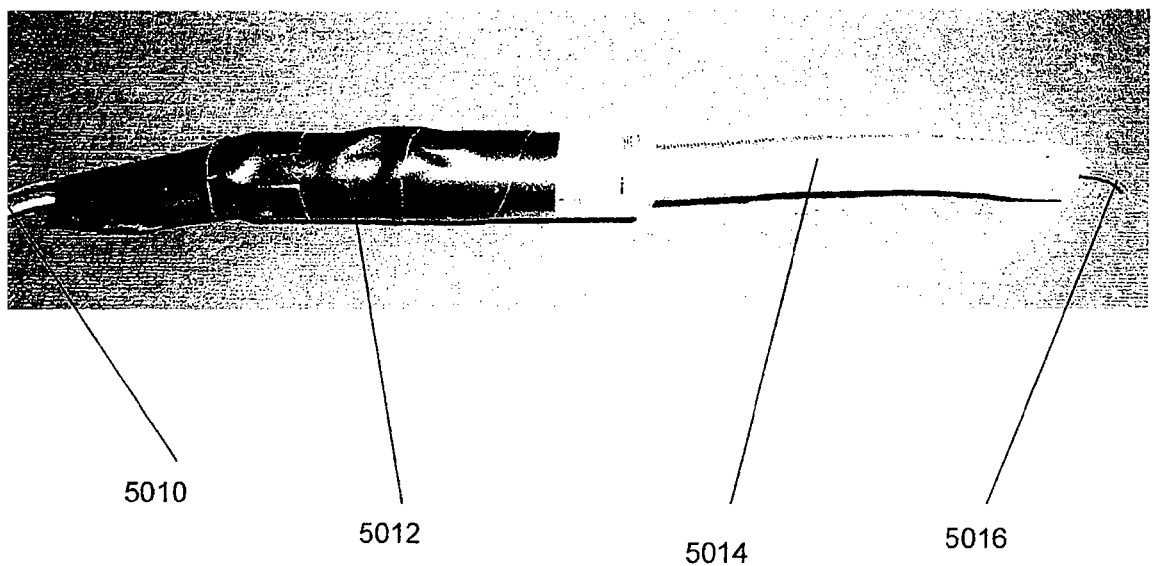
FIG. 47 is photograph of an exemplary prototype tongue implant device in accordance with one embodiment of the present invention.

FIG. 47 shows a photograph of an exemplary prototype tongue implant device in accordance with one embodiment of the present invention. Shown in FIG. 47 are the leads 5010 for powering the implant, the power/actuation portion 5012, the flexible middle section 5014 and the distal anchor 5016. It should be noted that the simple prototype device shown in FIG. 47 is for testing purposes and thus the novel implant device is not limited to the prototype of FIG. 47.

Figure 48:
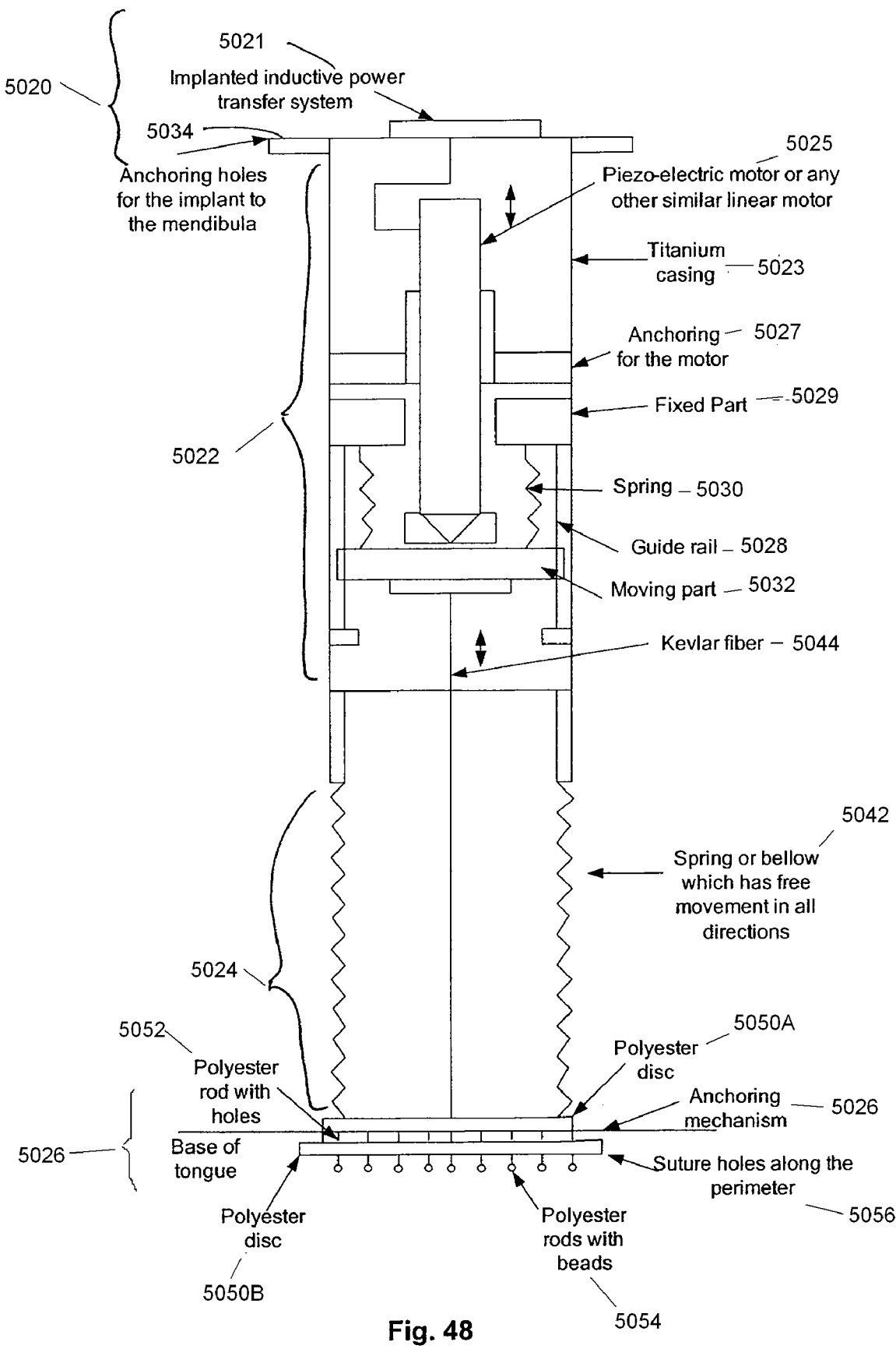
FIG. 48 is a simplified schematic drawing of an exemplary tongue implant device in accordance with another embodiment of the present invention.

FIG. 48 shows a simplified schematic drawing of an exemplary tongue implant device in accordance with another embodiment of the present invention. As shown in FIG. 48, the implant can include an anchor portion 5020 for securing the implant to the mandibula; a control portion 5022 for controlling the flexible portion 5024; a flexible portion 5024 and an anchor 5026 for securing the implant to the base of the tongue. As shown in FIG. 48, the actuation mechanism 5022 includes a small linear motor 5025 that is used to provide the linear actuation. For this purpose a Squiggle motor manufactured by New Scale Technologies can be used, but other suitable linear motors may also be used. Alternatively, in other embodiments, instead of motors other mechanisms such as smart active polymers/structures can also be used. As is shown in FIG. 48, the motor 5025 can be anchored to a titanium casing 5023 by using a combination of biocompatible epoxy and mechanical screw type anchoring through an internal anchoring mechanism 5027. The device of FIG. 48 can also have a guide mechanism 5028 which also incorporates a spring preload 5030. In operation, the motor 5025 pushes against a stainless steel block 5032 which is guided by the thin guide rails 5028. One or more springs 5030 can provide the pre-load against a fixed internal part 5029, such that under no load condition the motor shaft has an axial load to displace linearly. The power transmission system 5021 can be attached on top of the titanium casing such that it can be as close to the outside of the chin as possible to effect an inductive power coupling. The titanium casing 5023 has two or more tapped holes 5034 for anchoring it with biocompatible screws to the mandibula.

The tongue stabilizing mechanism or the middle flexible portion 5024 provides for three-dimensional flexibility for the implant. When powered the flexible portion is stiffened along the central longitudinal axis to hold the tongue in position so as not to block the airway. When not powered, the middle flexible portion 5024 provides for three-dimensional flexibility for the implant, so as to enable the patient to have adequate tongue movement during speaking and swallowing. The middle flexible portion 5024 can include a flexible spring, bellows, etched stent or a combination of the three as the mechanism for supporting the tongue. The middle flexible portion can be coated with an HA coating for preventing tissue in-growth. An important functionality of this mechanism is to permit flexible movement of the tongue in all degrees of freedom during its non active (e.g. non-powered) state. And when the actuator is active, it can tighten the tongue and stabilize it, preventing its multiple degrees of freedom. A tough but flexible material such as a Kevlar fiber 5044 can be used to connect the moving end of the actuation mechanism 5032 to the end of the stabilizing mechanism such that when the actuator moves back it pulls the fiber and stiffens the spring or bellow. It too can be coated with HA coating for preventing tissue growth.

The anchoring mechanism 5026 can include two concentric polyester discs 5050A-5050B with one 5050A connected with the tongue stabilizing mechanism with suture holes around its circumference. The second disc 5050B can also have suture holes 5056 around its circumference which are concentric with the holes in the first disc. Both discs can be connected by one or more polyester rods with holes 5052 for tissue in-growth. The disc further away from the middle flexible portion can be surgically inserted at the base of the tongue at a depth such that the second disc is in contact with the base of the tongue. The surgically implanted disc 5050B can also have one or more polyester rods with polyester beads 5054 to facilitate good tissue in-growth and hence good anchoring.

The tongue implant device in accordance with the embodiments of the present invention can have may alternative configurations, including one or more of the following described embodiments. In a first embodiment the flexible middle portion 5022 can be actuated by a combination of a piezoelectric actuator and a linear motor coupled with a cable to stiffen a spring or bellow structure. In a second embodiment, the flexible middle portion 5022 can be actuated by a combination of a Nitinol or other shape memory material obviating the need for a linear motor and cable arrangement. In a third embodiment, the flexible middle portion 5022 can be actuated by combination of an electro active polymer such as polypyrrole, obviating the need for a linear motor and cable arrangement. Preferably, the Nitinol or the polypyrrole material are of a non-toxic medical grade type. Alternatively, the non-medical grade implant materials are encased or coated in medical grade materials. Such coatings can include a hyaluronic acid, or a poly-Lysine acid coating. The power source for the actuation of the implant device can be a non-implanted power source that is inductively coupled with the power-actuation portion of the tongue implant.

Methods of Making Electroactive Polymer Element

In some embodiments, the EAP element is an IPMC strip which is made from a base material of an ionomer sheet, film or membrane. The ionomer sheet is formed using ionomer dispersion.

IPMC is made from the base ionomer of, for example, polyethylene, polystyrene, polytetrafluoroethylene, polyvinylidene fluoride (PVDF) (e.g., KYNAR® and KYNAR Flex®, from ATOFINA, Paris, France, and SOLEF®, from Solvay Solexis S.A., Brussels, Belgium), hydrophilic-PVDF (h-PVDF), polyfluorosulfonic acid based membranes like NAFION® (from E.I. Du Point de Nemours and Company, Wilmington, Del.), polyaniline, polyacrylonitrile, cellulose, cellulose acetates, regenerated cellulose, polysulfone, polyurethane, and combinations thereof. The conductive material that is deposited on the ionomer can be gold, platinum, silver, palladium, copper, graphite, conductive carbon, or combinations thereof. Conductive material is deposited on the ionomer either by electrolysis process, vapor deposition, sputtering, electroplating, or combination of processes.

The IPMC is cut into the desired implant shape for the EAP element. The electrical contact (e.g., anode and cathode wires for EAP element) is connected to the IPMC surfaces by, for example, soldering, welding, brazing, potting using conductive adhesives, or combinations thereof. The EAP element is configured, if necessary, into specific curved shapes using mold and heat setting processes.

In some embodiments, the EAP element is insulated with electrical insulation coatings. Also, the EAP element can be insulated with coatings that promote cell growth and minimize fibrosis, stop cell growth, or kill nearby cells. The insulation can be a biocompatible material. The EAP element is coated with polymers such as polypropylene, poly-L-lysine, poly-D-lysine, polyethylene glycol, polyvinyl alcohol, polyvinyl acetate, polymethyl methacrylate, or combinations thereof. The EAP element can also be coated with hyaluronic acid. The coating is applied to the device by standard coating techniques like spraying, electrostatic spraying, brushing, vapor deposition, dipping, etc.

In one example, a perfluorosulfonate ionomer, PVDF or h-PVDF sheet is prepared for manufacturing the EAP element. In an optional step, the sheet is roughened on both sides using, for example, about 320 grit sand paper and then about 600 grit sand paper; then rinsed with deionized water; then submerged in isopropyl alcohol (IPA); subjected to an ultrasonic bath for about 10 minutes; and then the sheet is rinsed with deionized water. The sheet is boiled for about 30 minutes in hydrochloric acid (HCL). The sheet is rinsed and then boiled in deionized water for about 30 minutes. The sheet is then subject to ion-exchange (i.e., absorption). The sheet is submerged into, or otherwise exposed to, a metal salt solution at room temperature for more than about three hours. Examples of the metal salt solution are tetraammineplatinum chloride solution, silver chloride solution, hydrogen tetrachloroaurate, tetraamminepalladium chloride monohydrate or other platinum, gold, silver, carbon, copper, or palladium salts in solution. The metal salt solution typically has a concentration of greater than or equal to about 200 mg/100 ml water. 5% ammonium hydroxide solution is added at a ratio of 2.5 ml/100 ml to the tetraammineplatinum chloride solution to neutralize the solution. The sheet is then rinsed with deionized water. Primary plating is then applied to the sheet. The sheet is submerged in water at about 40° C. 5% solution by weight of sodium borohydride and deionized water is added to the water submerging the sheet at 2 ml/180 ml of water. The solution is stirred for 30 minutes at 40° C. The sodium borohydride solution is then added to the water at 2 ml/180 ml of water and the solution is stirred for 30 minutes at 40° C. This sodium borohydride adding and solution stirring is performed six times total. The water temperature is then gradually raised to 60° C. 20 ml of the sodium borohydride solution is then added to the water. The solution is stirred for about 90 minutes. The sheet is then rinsed with deionized water, submerged into 0.1N HCl for an hour, and then rinsed with deionized water.

In some embodiments, the sheet receives second plating. The sheet is submerged or otherwise exposed to a tetraammineplatinum chloride solution at a concentration of about 50 mg/100 ml deionized water. 5% ammonium hydroxide solution is added at a rate of 2 ml/100 ml of tetraammineplatinum chloride solution. 5% by volume solution of hydroxylamine hydrochloride in deionized water is added to the tetraammineplantium chloride solution at a ratio of 0.1 of the volume of the tetraammineplatinum chloride solution. 20% by volume solution of hydrazine monohydrate in deionized water is added to the tetraammineplatinum chloride solution at a ratio of 0.05 of the volume of the tetraammineplantinum chloride solution. The temperature is then set to about 40° C. and the solution is stirred.

A 5% solution of hydroxylamine hydrochloride is then added at a ratio of 2.5 m/100 ml of tetraammineplatinum chloride solution. A 20% solution of hydrazine monohydrate solution is then added at a ratio of 1.25 ml/100 ml tetraammineplatinum chloride solution. The solution is stirred for 30 minutes and the temperature set to 60° C. The above steps in this paragraph can be repeated three additional times. The sheet is then rinsed with deionized water, boiled in HCl for 10 minutes, rinsed with deionized water and dried.

In some embodiments, the polymer base is dissolved in solvents, for example dimethyl acetamide, acetone, methylethyle ketone, toluene, dimethyl carbonate, diethyl carbonate, and combinations thereof. The solvent is then allowed to dry, producing a thin film. While the solution is wet, a low friction, (e.g., glass, Teflon) plate is dipped into the solution and removed. The coating on the plate dries, creating a think film. The plate is repeatedly dipped into the solution to increase the thickness of the film.

Polyvinyl alcohol, polyvinyl pyrrolidone, polyinyl acetate or combinations thereof can be added to a PVDF solution before drying, thus contributing hydrophilic properties to PVDF and can improve ion migration through the polymer film during manufacture. Dye or other color pigments can be added to the polymer solution.

Method of Using

Figure 25:
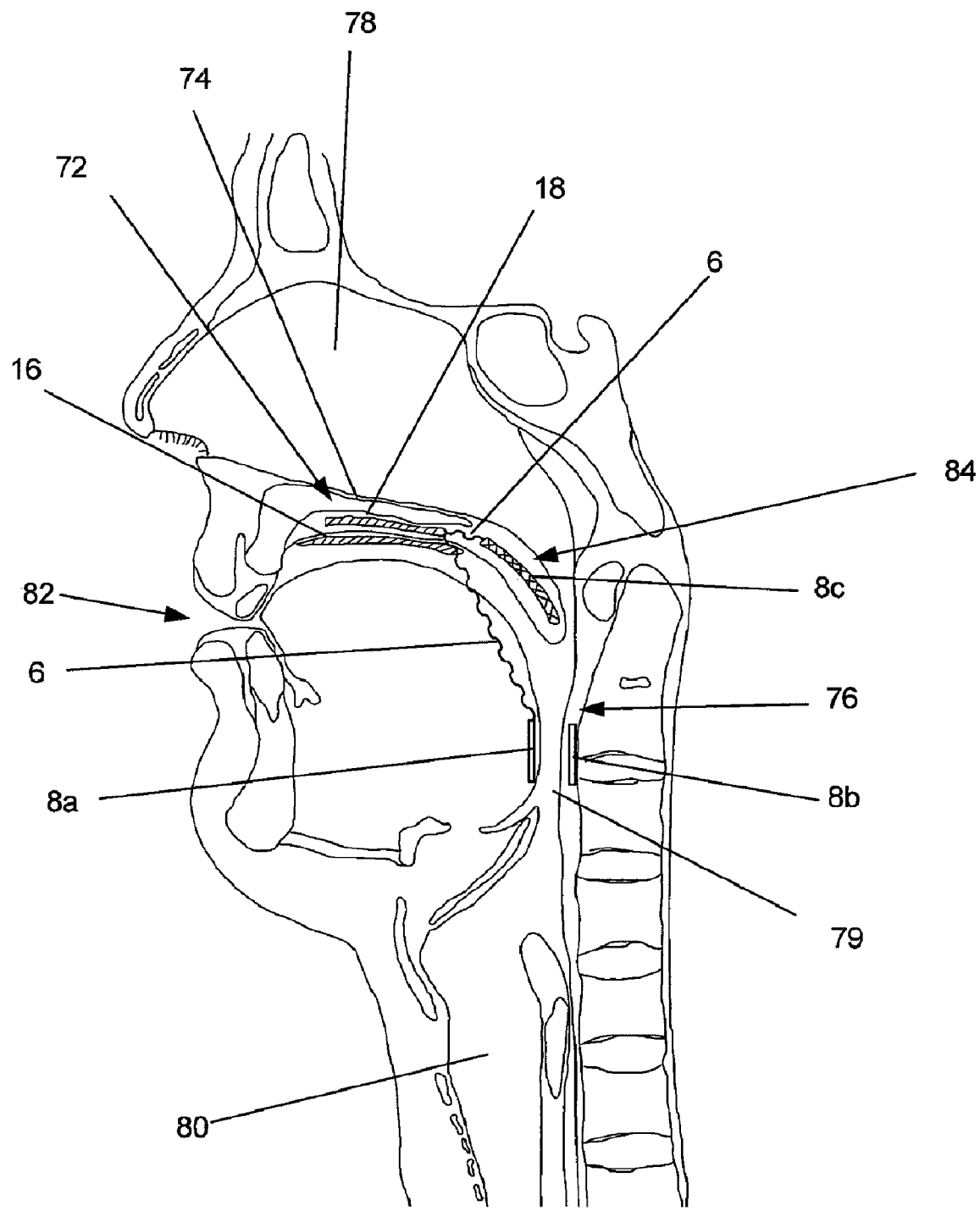
FIG. 25 shows a sagittal section through a head of a subject illustrating an embodiment of a method for using the airway implant device.

FIG. 25 illustrates an embodiment of a method of the airway implant device of the present invention. In this embodiment, the first inductor 18 is implanted in the mouth roof 72, for example in or adjacent to the hard palate 74. Wire leads 6 connect the first inductor 18 to the deformable elements 8a, 8b, and 8c. A first deformable element 8a is implanted in the base of the tongue at the pharynx wall 76. A second deformable element 8b is integral with the first deformable element 8a (e.g., as two sections of a hollow cylindrical deformable element 8, such as shown in FIG. 17). The first and second deformable elements 8a and 8b can be separate and unattached elements. The third deformable element 8c is implanted in the uvula and/or soft palate 84. The deformable elements 8 can also be implanted in the wall of the nasal passages 78, higher or lower in the pharynx 79, such as in the nasal pharynx, in the wall of the trachea 80, in the larynx (not shown), in any other airway, or combinations thereof. The second inductor 16 is worn by the patient in the mouth 82. The second inductor 16 is connected to an integral or non-integral power supply. The second inductor 16 comprises one or multiple induction coils. The second inductor 16 inductively transmits RF energy to the first inductor 18. The first inductor 18 changes the RF energy into electricity. The first inductor 18 sends a charge or current along the wire leads 6 to the deformable elements 8a, 8b, and 8c. The deformable elements 8a, 8b, and 8c are energized by the charge or current. The energized deformable elements 8a, 8b, and 8c increase the stiffness and/or alter the shape of the airways. The energized deformable elements 8a, 8b, and 8c modulate the opening of the airways around which the deformable elements 8a, 8b, and 8c are implanted. The non-energized deformable elements 8a, 8b, and 8c are configured to conform to the airway around which the deformable elements 8a, 8b, and 8c are implanted. The non-energized deformable elements 8a, 8b, and 8c are flexible and soft.

Figure 26:
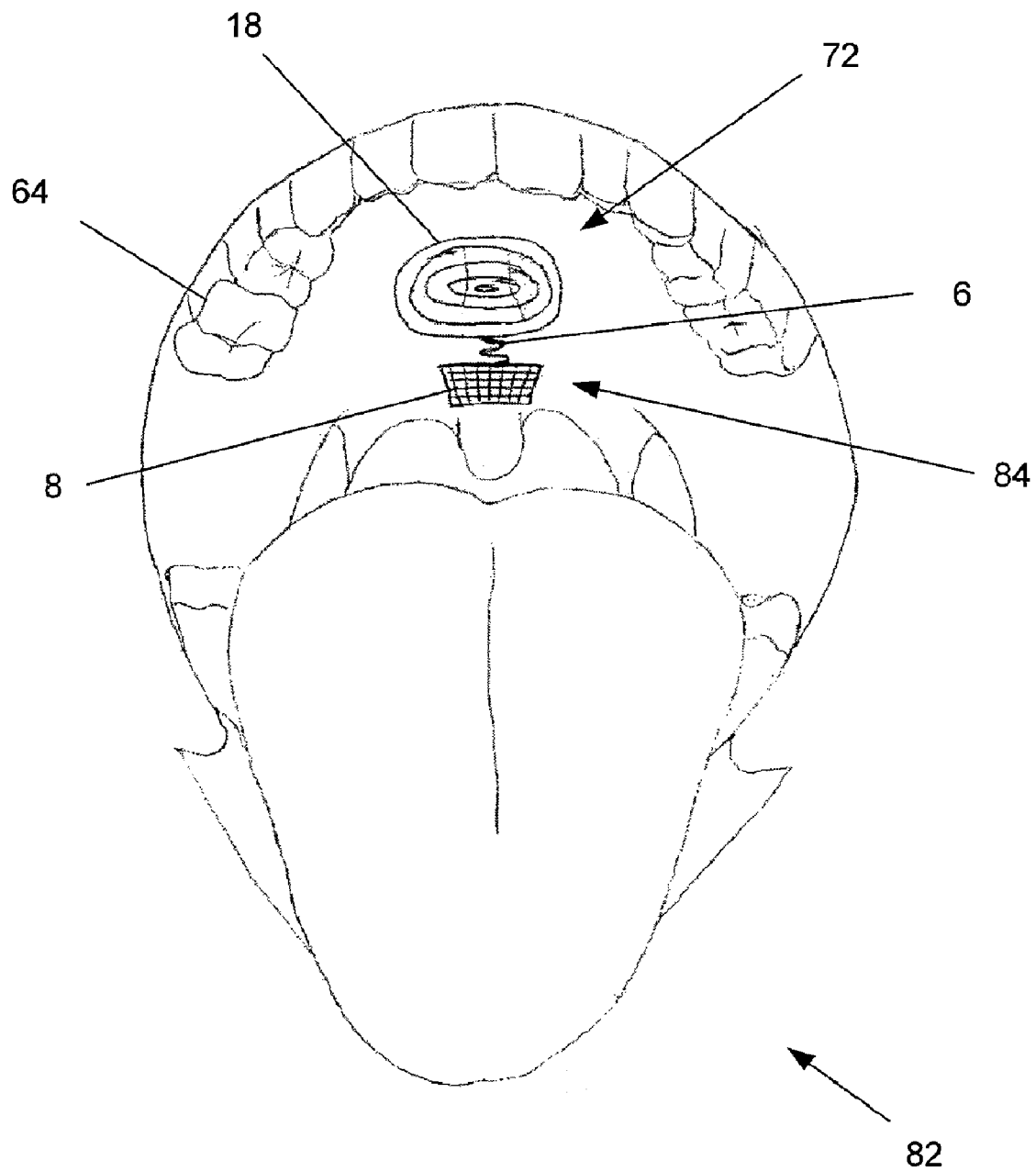
FIG. 26 illustrates an anterior view of the mouth with see-through mouth roofs to depict an embodiment of a method for using the airway implant device.
Figure 27:
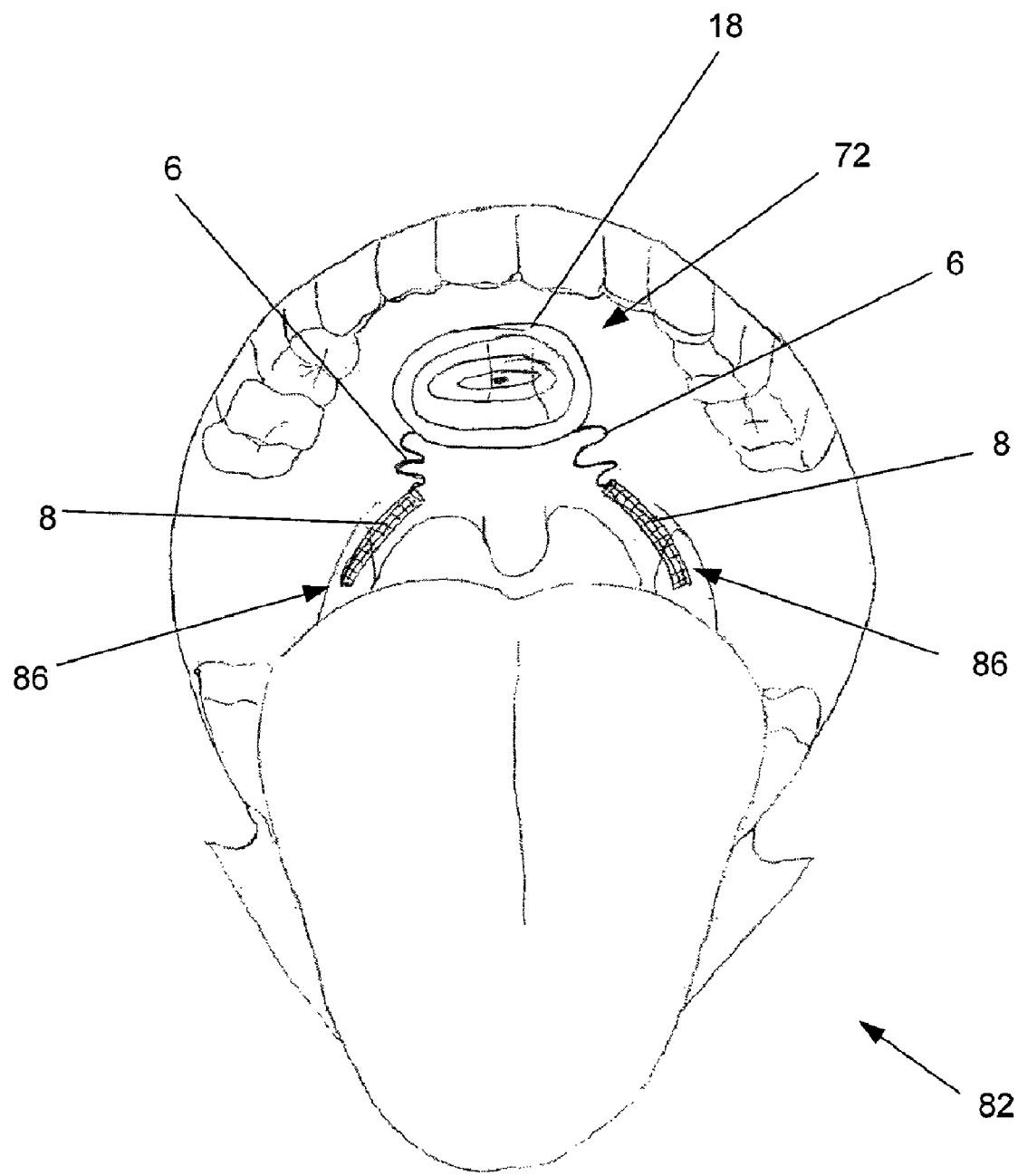
FIG. 27 illustrates an anterior view of the mouth with see-through mouth roofs to depict an embodiment of a method for using the airway implant device.
Figure 28:
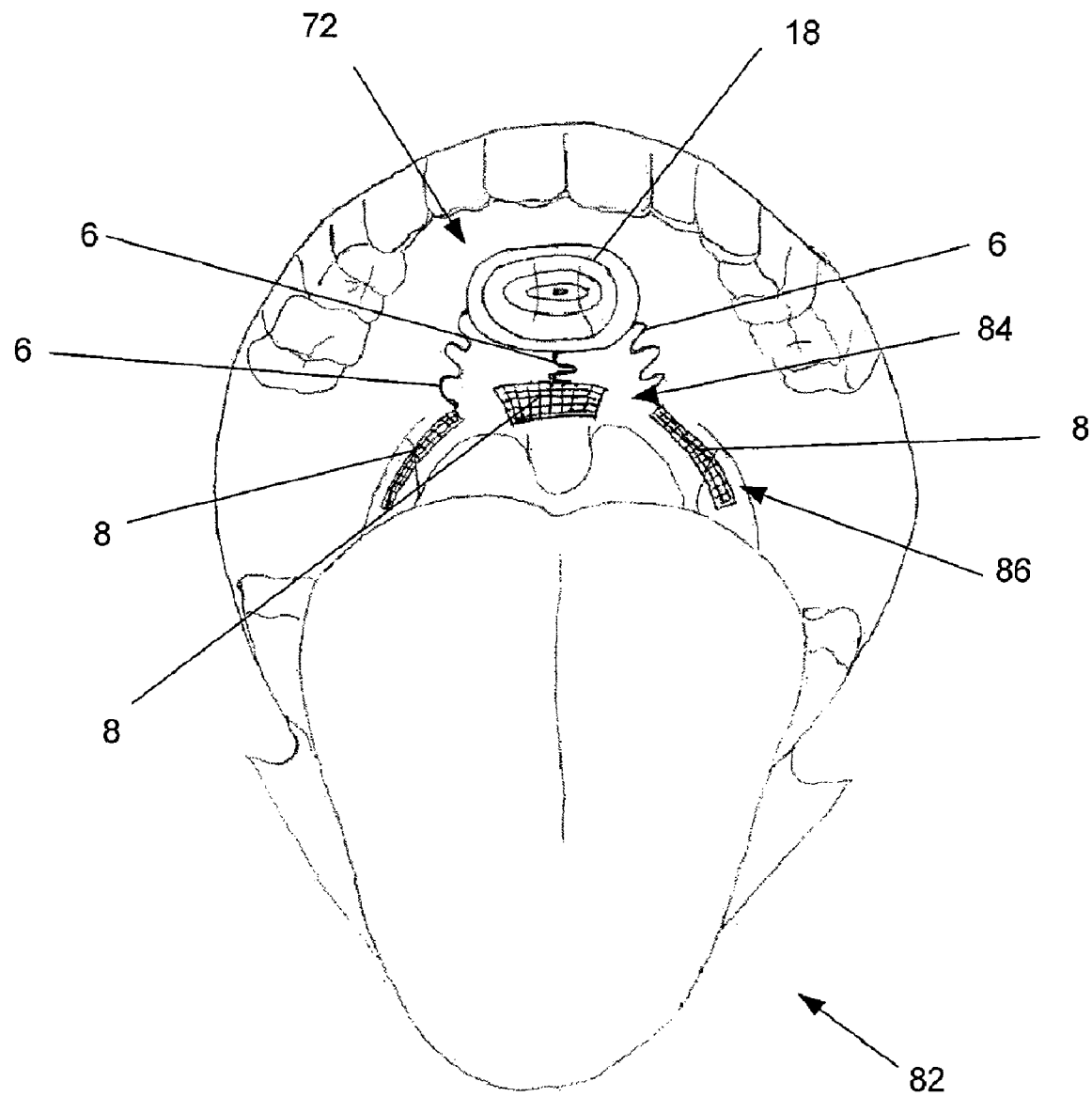
FIG. 28 illustrates an anterior view of the mouth with see-through mouth roofs to depict an embodiment of a method for using the airway implant device.
Figure 29:
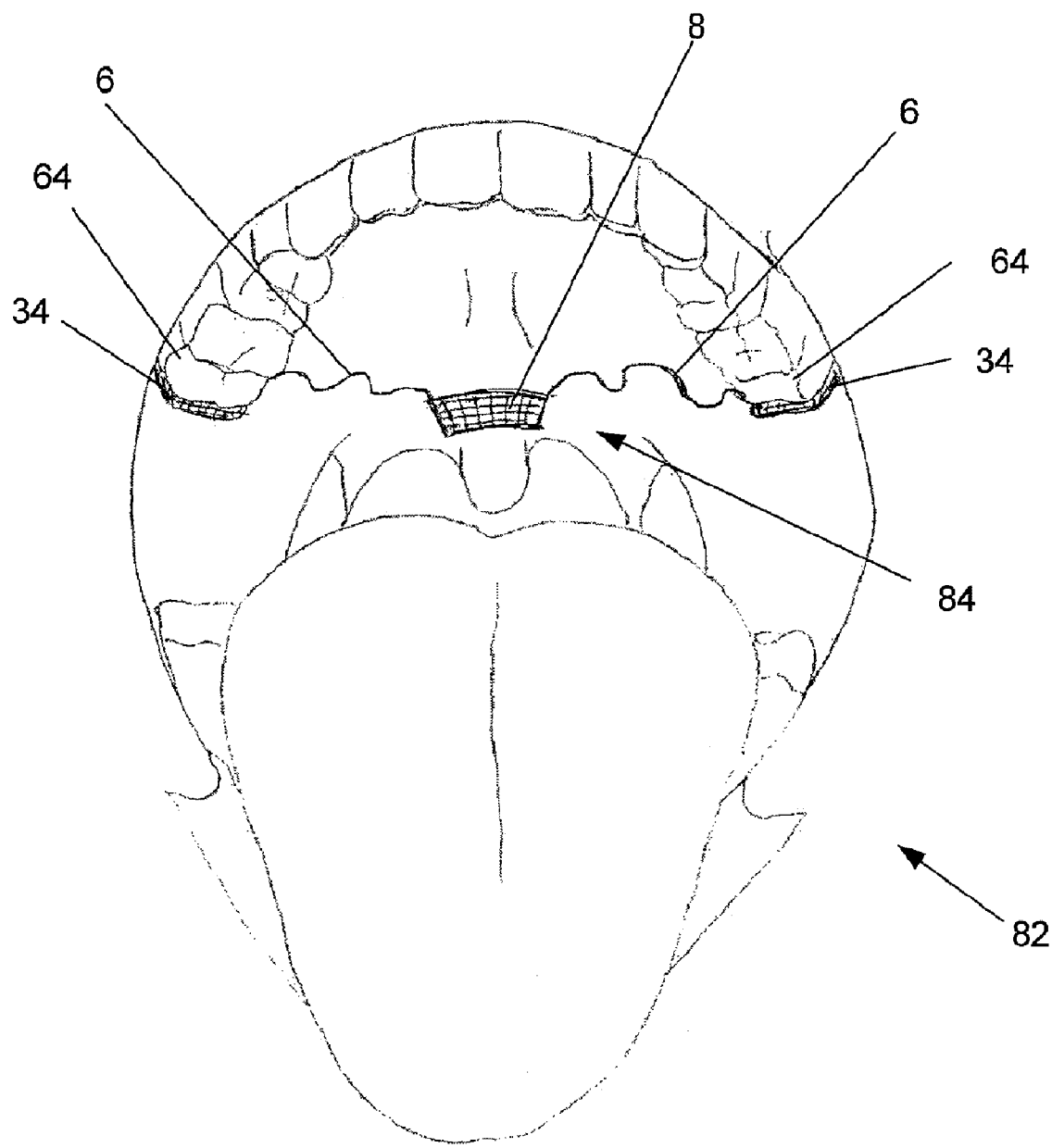
FIG. 29 illustrates an anterior view of the mouth with see-through mouth roofs to depict an embodiment of a method for using the airway implant device.

FIG. 26 illustrates another embodiment of the invention. In this embodiment, the first inductor 18 is implanted in the mouth roof 72 and attached to a deformable element 8 via the wire lead 6. The deformable element 8 is preferably in the soft palate 84. In another embodiment, FIG. 27 illustrates that the first inductor 18 is implanted in the mouth roof 72 and attached to two deformable elements 8 via two wire leads 6. The deformable elements 8 are implanted in side walls 86 of the mouth 82. In yet another embodiment, as illustrated in FIG. 28, the first inductor 18 is implanted in the mouth roof 72 and attached to three deformable elements 8 via three wire leads 6. The deformable elements 8 are implanted in the soft palate 84 and the side walls 86 of the mouth 82. FIG. 29 illustrates an embodiment in which the first conductors (not shown, e.g., the tooth sockets), are attached to, and in conductive electrical communication with, the second conductors. The retainer 66, such as shown in FIG. 23, can be worn by the patient to energize the deformable element 8. The tooth sockets are removably attached to the first conductors 34. The first conductors 34 are dental fillings, conductive posts adjacent to and/or through the teeth 64.

Figure 33:
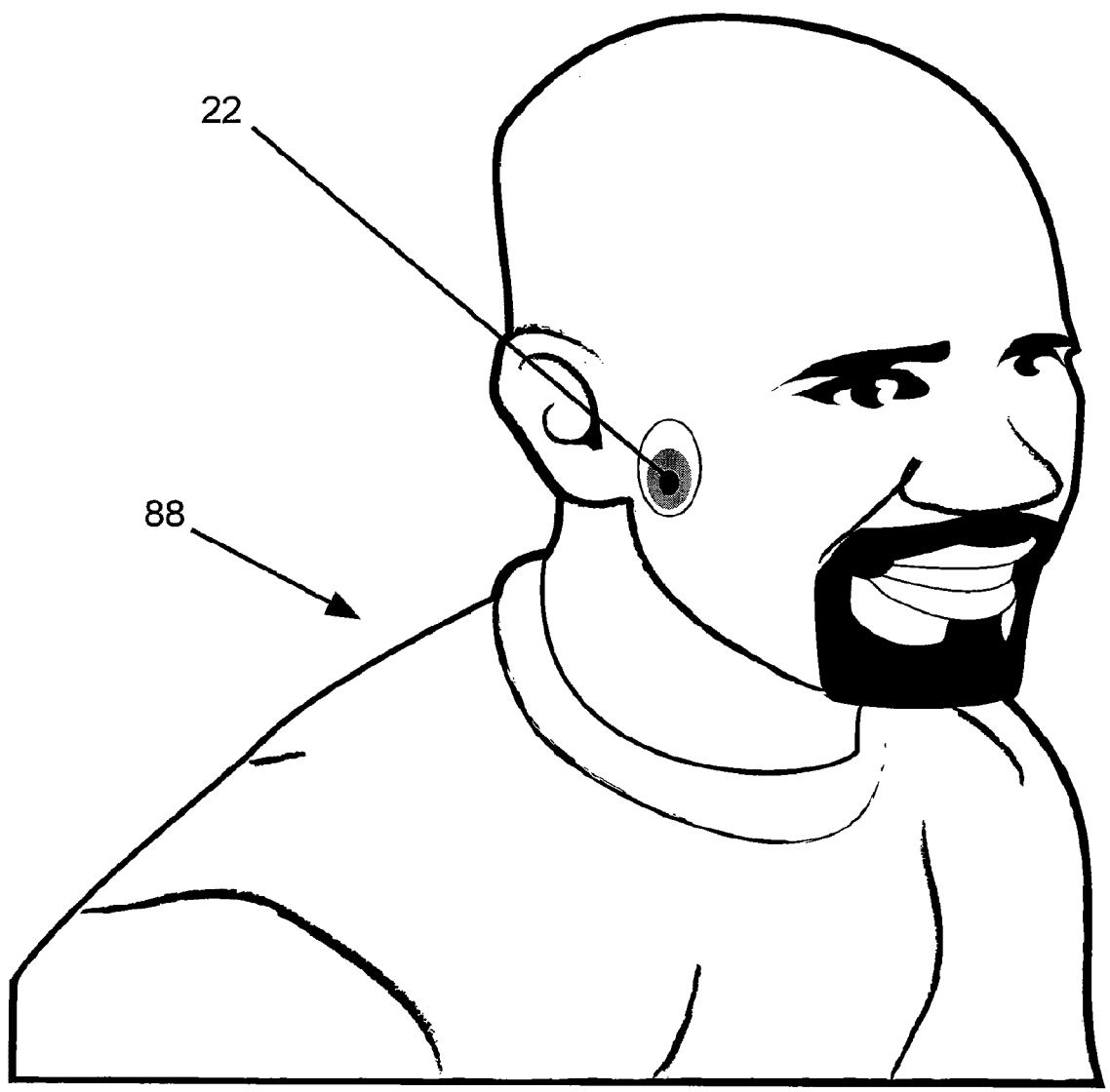
FIG. 33 illustrates an embodiment in which a patient wears the non-implanted portion of the device on the cheeks.

FIG. 33 illustrates an embodiment in which a patient 88 has the first transducer (not shown) implanted in the patient's cheek and wears the non-implanted portion 22, such as shown in FIG. 24, on the outside of the patient's cheek. The non-implanted portion 22 energizes the implanted portion (not shown).

Figure 34A:
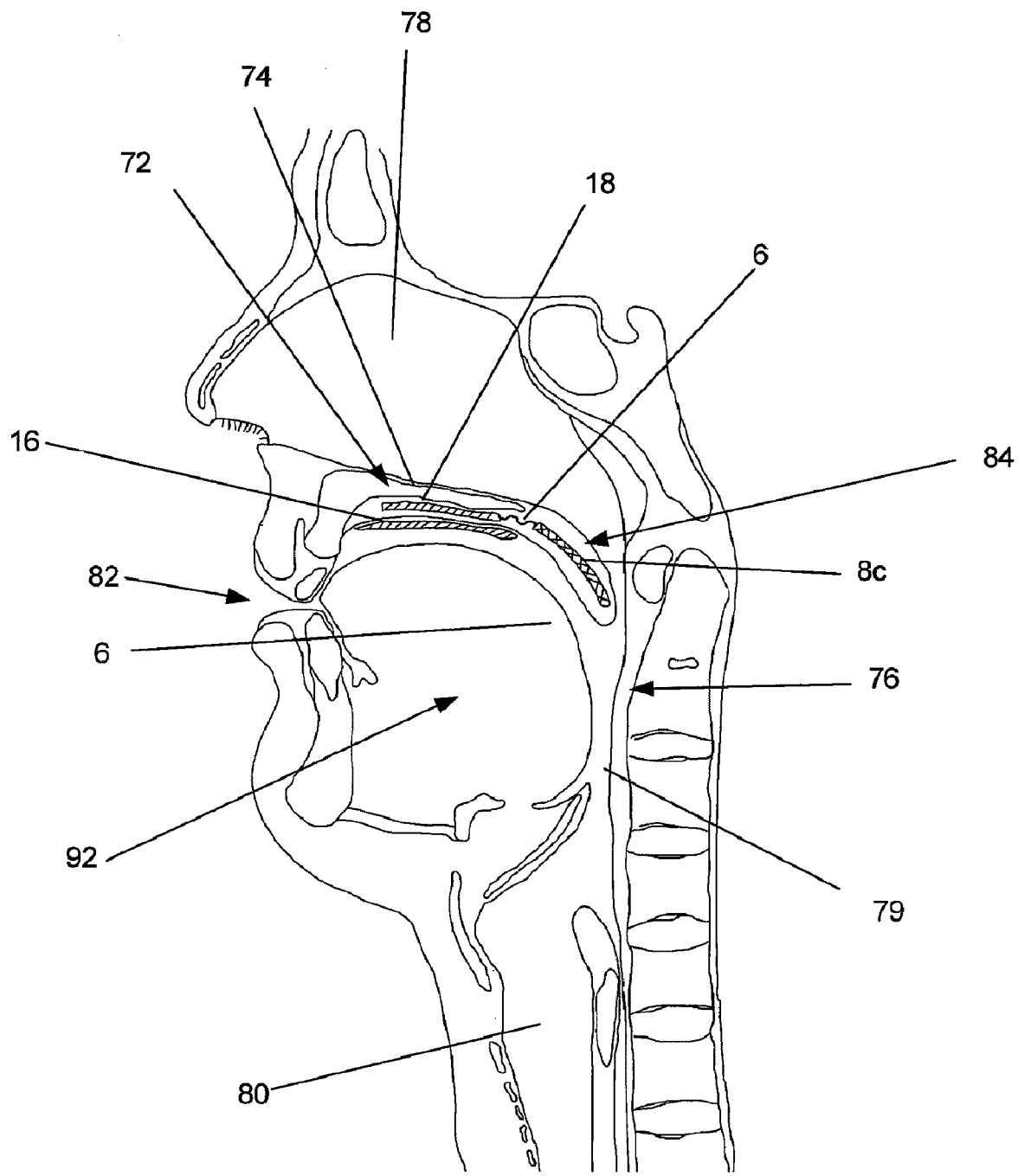
FIG. 34A-34B illustrates an embodiment of a method of the invention with the airway implant in the soft palate.
Figure 34B:
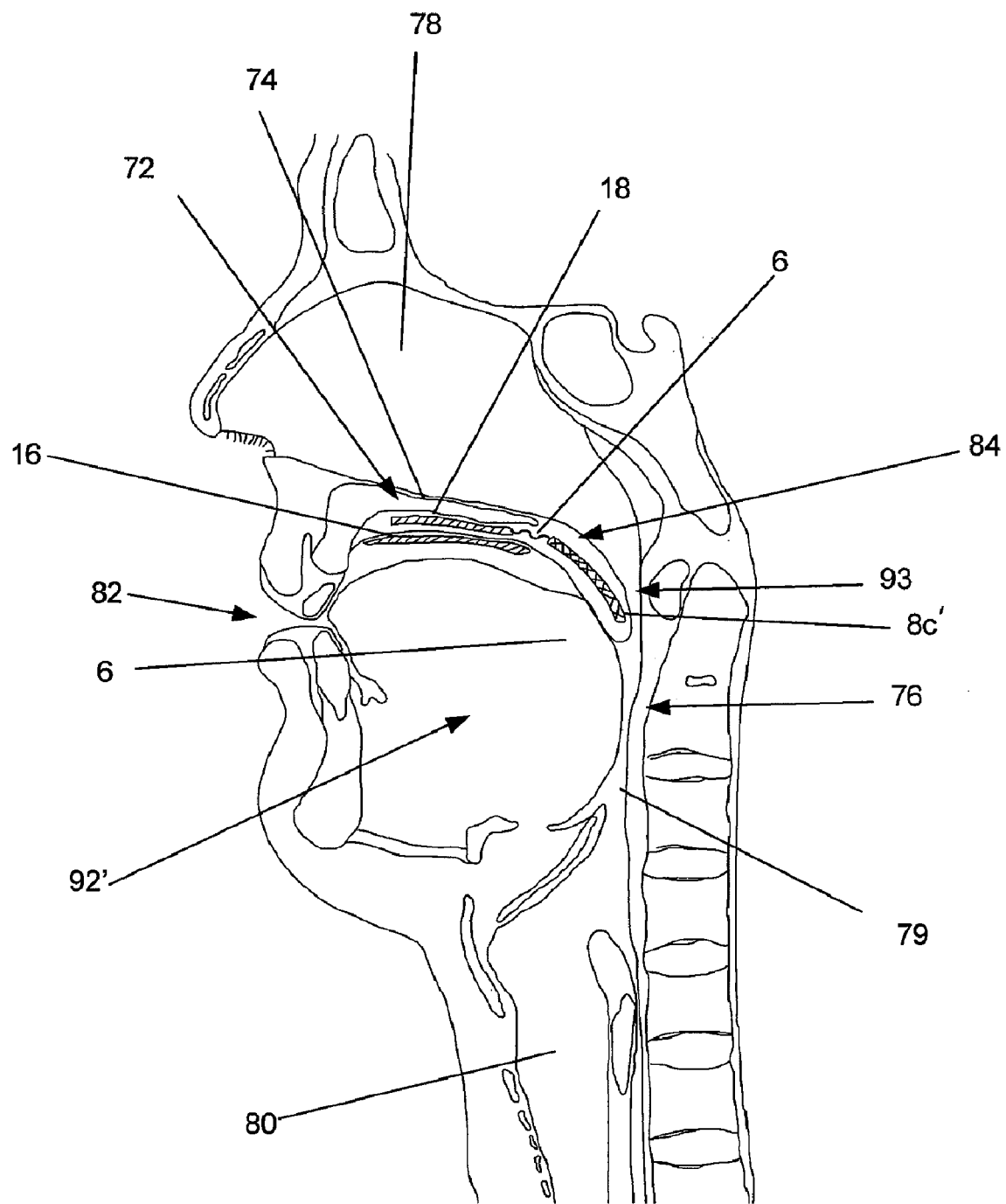

FIGS. 34-36 depict some of the ways in which the implant devices function to open the airways. FIGS. 34A and 34B depict a side view of a patient with a soft palate implant 8c and a non-implanted portion of the device, with a second inductor 16, which in this case is a wearable mouth piece. The wearable mouth piece includes a transmitter coil, a power source, and other electronics, which are not depicted. Also, shown is a first inductor 18. The implant device has the ability to sense and deflect the tongue so as to open the airway. FIG. 34A depicts the tongue 92 in its normal state. During sleep, when the tongue collapses 92', as shown in FIG. 34B, the deformable element 8c' senses the collapsed tongue and is energized via the mouthpiece and first inductor and it stiffens to push away the tongue from the airway and keeps the airway open. This opening of the airway can be partial or complete. In some embodiments, particularly the embodiments without the sensor, the implant is powered when the patient is asleep such that the deformable element 8 is energized and keeps the collapsed tongue away from the airway.

Figure 35A:
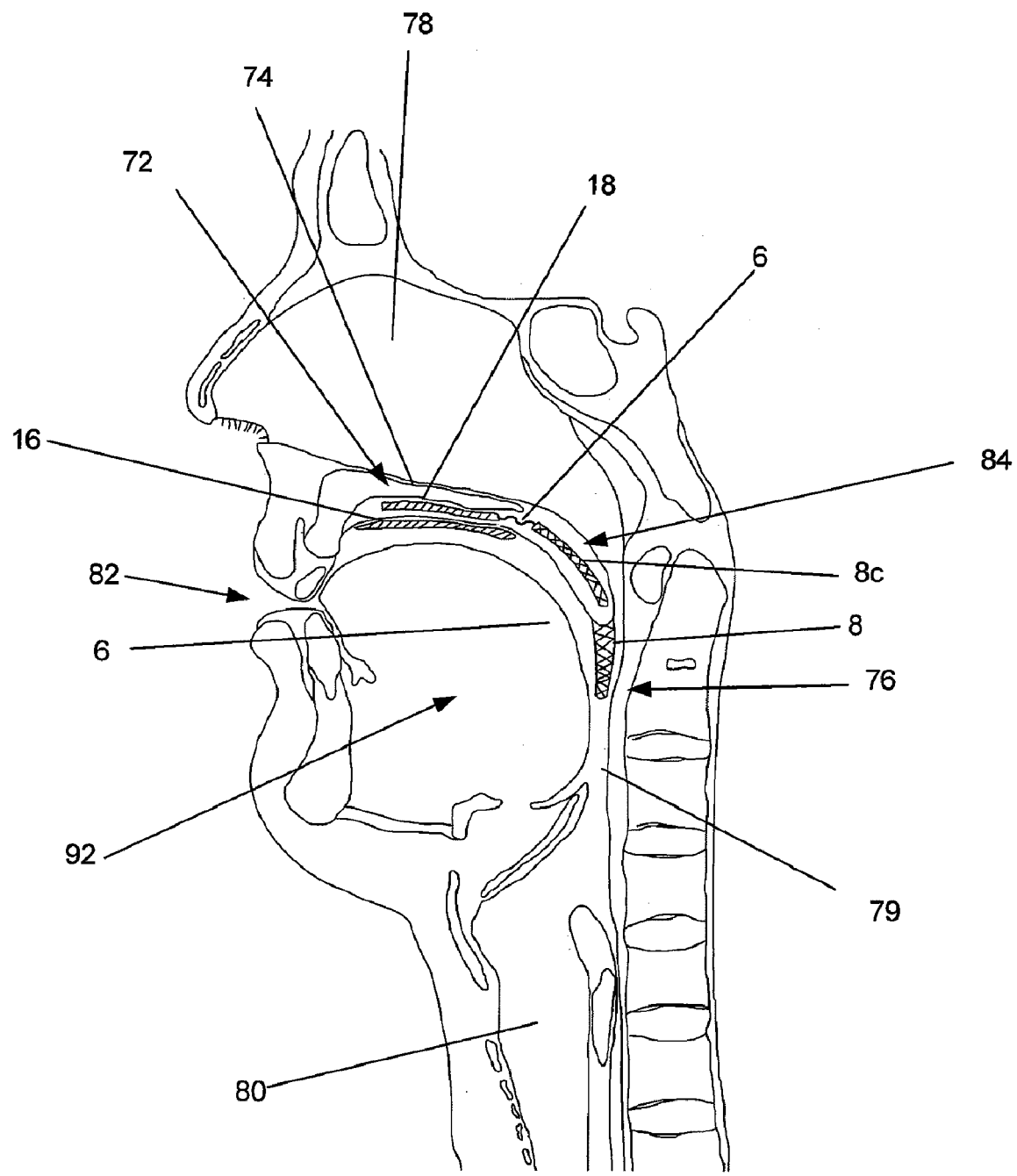
FIG. 35A-35B illustrates an embodiment of a method of the invention with the airway implants in the soft palate and lateral pharyngeal walls.
Figure 35B:
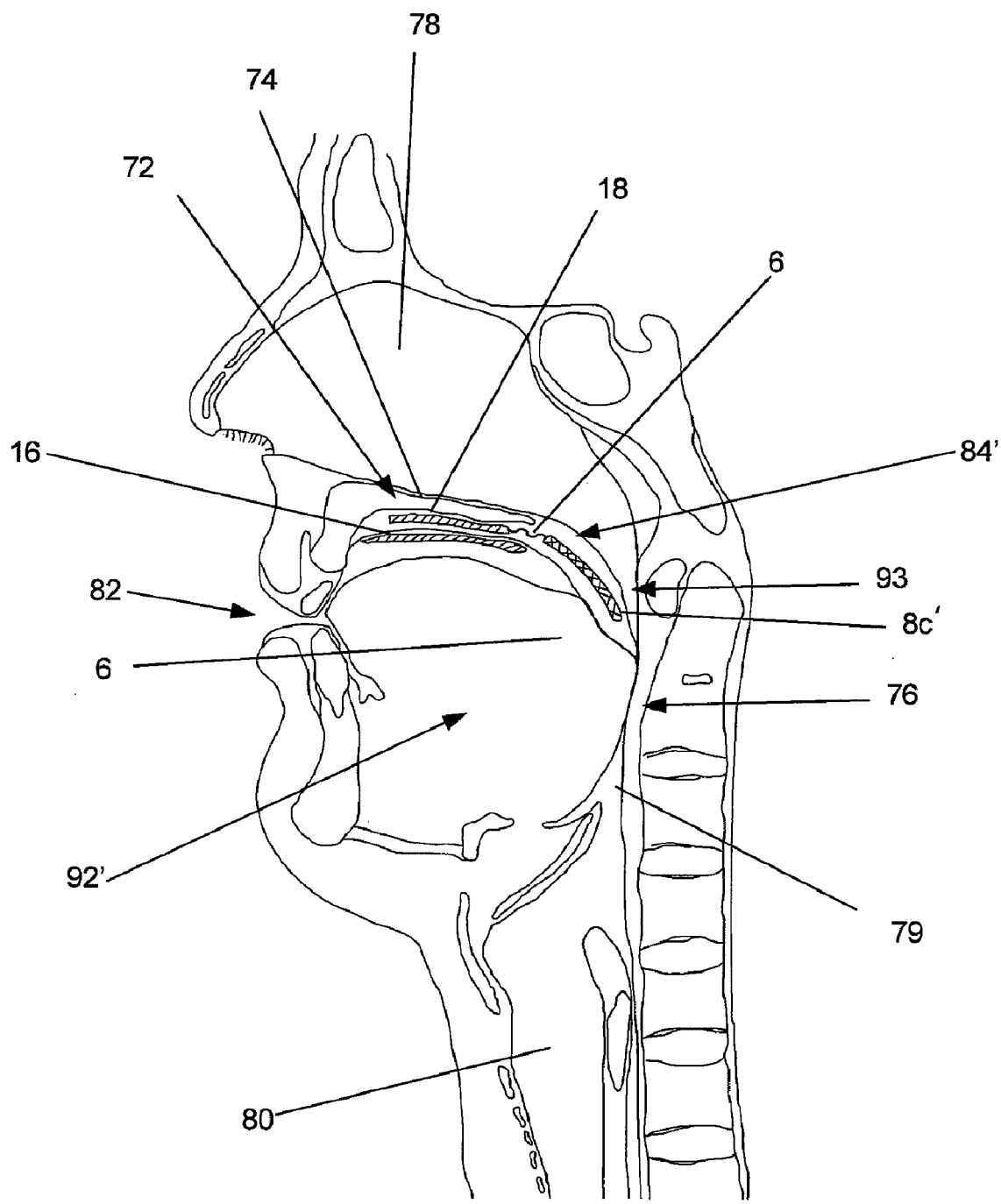
Figure 36A:
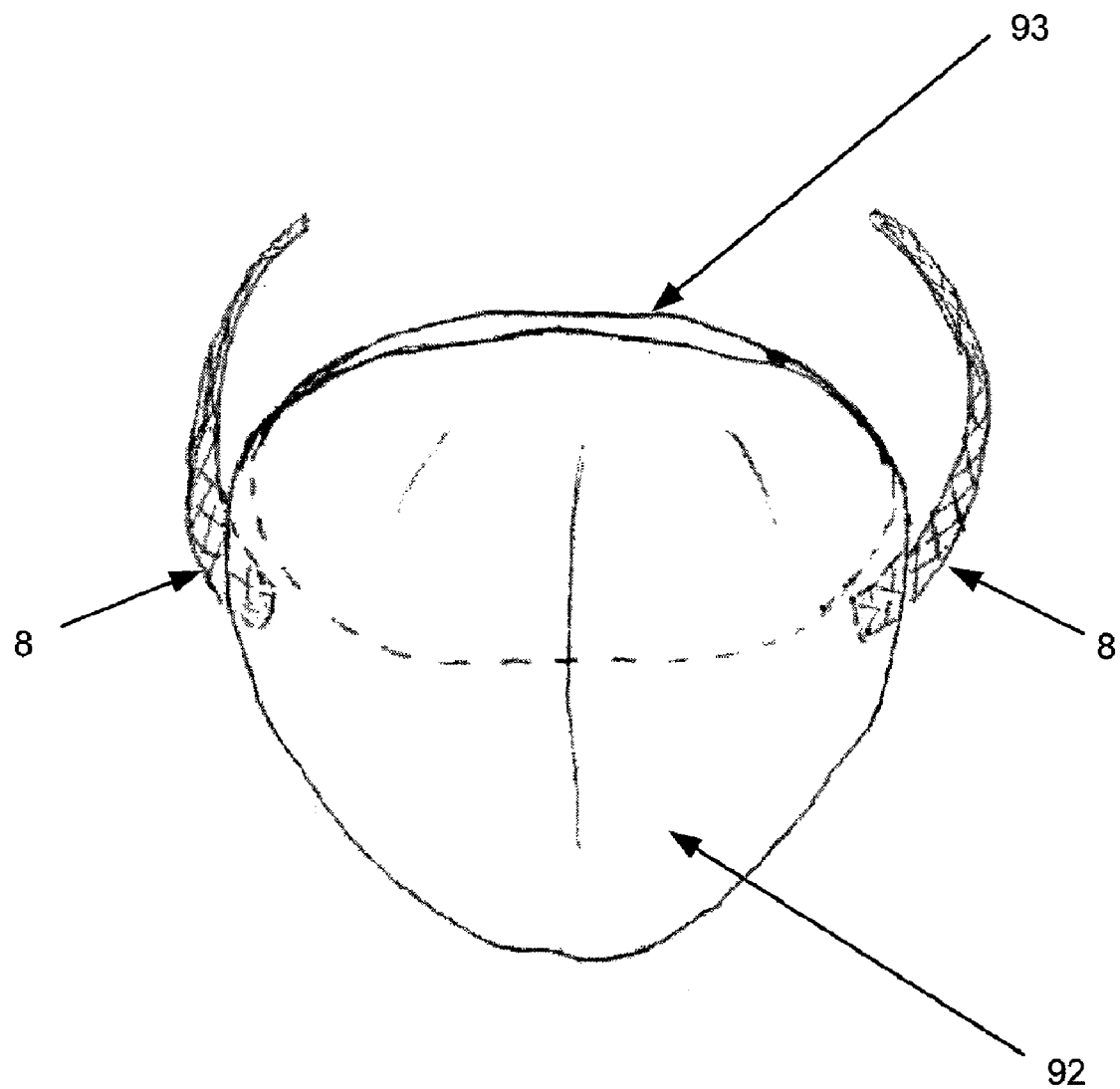
FIG. 36A-36B illustrates an embodiment of a method of the invention with the airway implants in the lateral pharyngeal walls.
Figure 36B:
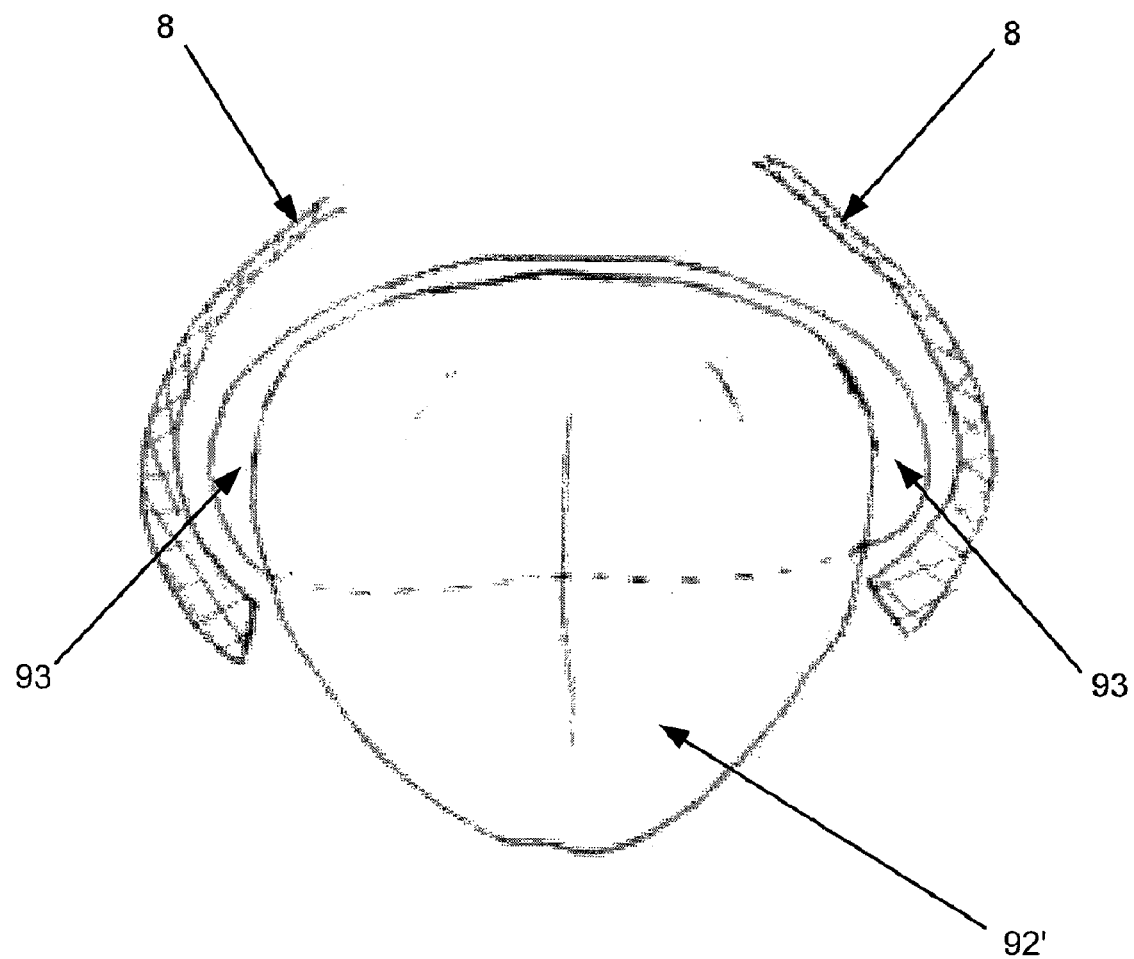

FIGS. 35 and 36 depict an embodiment of keeping the airways open with lateral wall implants. FIG. 35A shows a side view of a patient's face with a deformable element 8 located in the lateral wall of the airway. FIG. 35A depicts the tongue 92 in its normal state. FIG. 35B depicts the tongue 92' in a collapsed state. When the tongue is in this state or before it goes into the collapsed state the deformable element 8 is energized so as to stretch the lateral walls and open the airway, as shown in FIG. 36B. FIGS. 36A and 36B are a view of the airway as seen through the mouth of patient. FIG. 36 A depicts the deformable elements 8 in a non-energized state and the tongue in a non-collapsed state. When the tongue collapses or it has a tendency to collapse, such as during sleep, the deformable element 8 is energized and airway walls are pushed away from the tongue and creates an open air passageway 93. This embodiment is particularly useful in obese patients.

Airway Diseases

During sleep, the muscles in the roof of the mouth (soft palate), tongue and throat relax. If the tissues in the throat relax enough, they vibrate and may partially obstruct the airway. The more narrowed the airway, the more forceful the airflow becomes. Tissue vibration increases, and snoring grows louder. Having a low, thick soft palate or enlarged tonsils or tissues in the back of the throat (adenoids) can narrow the airway. Likewise, if the triangular piece of tissue hanging from the soft palate (uvula) is elongated, airflow can be obstructed and vibration increased. Being overweight contributes to narrowing of throat tissues. Chronic nasal congestion or a crooked partition between the nostrils (deviated nasal septum) may be to blame.

Snoring may also be associated with sleep apnea. In this serious condition, excessive sagging of throat tissues causes your airway to collapse, preventing breathing. Sleep apnea generally breaks up loud snoring with 10 seconds or more of silence. Eventually, the lack of oxygen and an increase in carbon dioxide signal causes the person to wake up, forcing the airway open with a loud snort.

Obstructive sleep apnea occurs when the muscles in the back of the throat relax. These muscles support the soft palate, uvula, tonsils and tongue. When the muscles relax, the airway is narrowed or closed during breathing in, and breathing is momentarily cut off. This lowers the level of oxygen in the blood. The brain senses this decrease and briefly rouses the person from sleep so that the airway can be reopened. Typically, this awakening is so brief that it cannot be remembered. Central sleep apnea, which is far less common, occurs when the brain fails to transmit signals to the breathing muscles.

Thus, it can be seen that airway disorders, such as sleep apnea and snoring, are caused by improper opening of the airway passageways. The devices and methods described herein are suitable for the treatment of disorders caused by the improper opening of the air passageways. The devices can be implanted in any suitable location such as to open up the airways. The opening of the passageways need not be a complete opening and in some conditions a partial opening is sufficient to treat the disorder.

In addition to air passageway disorders, the implants disclosed herein are suitable for use in other disorders. The disorders treated with the devices include those that are caused by improper opening and/or closing of passageways in the body, such as various locations of the gastro-intestinal tract or blood vessels. The implantation of the devices are suitable for supporting walls of passageways The devices can be implanted in the walls of the gastro-intestinal tract, such as the esophagus to treat acid reflux. The gastro-intestinal tract or blood vessel devices can be used in combination with the sensors described above. Also, the implants and/or sphincters can be used for disorders of fecal and urinary sphincters. Further, the implants of said invention can be tailored for specific patient needs.

As will be understood by those skilled in the art, the present invention may be embodied in other specific forms without departing from the essential characteristics thereof. Those skilled in the art will recognize, or be able to ascertain using no more than routine experimentation, many equivalents to the specific embodiments of the invention described herein. Such equivalents are intended to be encompassed by the following claims.

What is claimed is:

1. An implant for stabilizing the tongue, comprising:
a first anchoring portion for securing a first end of the implant with the mandibula;
a second anchoring portion configured to connect the implant with the base of the tongue;
a control portion disposed between and connecting the first anchoring portion with the second anchoring portion, the control portion configured to selectively reduce a distance between the first and second anchoring portions;
a flexible portion having a substantially tubular-shaped body with proximal and distal ends and an internal passage spanning there between, the flexible portion connected at its proximal end with the control portion and at its distal end with the second anchoring portion, said flexible portion having three-dimensional flexibility in a first state and said flexible portion having a lesser three-dimensional flexibility in a second state, said flexible portion being selectively switchable between said first and second state by said control portion, wherein a portion of the control portion is connected with the second anchoring portion and is routed through the internal passage of the flexible portion.

2. The implant of claim 1 wherein said second anchoring portion comprises a first disc connected with the distal end of said flexible portion and a second disc connectible with the base of the tongue.

3. The implant of claim 2 wherein said first and second discs comprise suture holes disposed around their circumferences.

4. The implant of claim 2 wherein said first and second discs further comprise polyester rods having holes extending from the flat surfaces of the discs.

5. The implant of claim 1 wherein said first anchoring portion includes an anchoring bracket.

6. The implant of claim 1 wherein said control portion comprises a spring-biased linear motor coupled with a flexible fiber, said fiber connected at its proximal end with a load movable by said motor and said fiber connected at its distal end with said second anchoring portion, said flexible fiber at least partially disposed within the internal passage of the flexible portion and configured to impart an axial load on said flexible portion.

7. The implant of claim 1 wherein said control portion is powered by a non-implanted inductively coupled power source.

8. The implant of claim 1 wherein said control portion comprises a shape memory alloy.

9. The implant of claim 1 wherein said control portion comprises an electro active polymer.

10. The implant of claim 1 wherein said flexible portion comprises a flexible helical spring.

11. The implant of claim 1 wherein said flexible portion comprises a bellows structure.

12. The implant of claim 1 wherein said flexible portion comprises an etched stent-like portion.

13. The implant of claim 1 wherein said flexible portion is coated with a hyaluronic acid coating.

* * * * *